(12) United States Patent
Marfat et al.

(10) Patent No.: US 7,091,197 B2
(45) Date of Patent: Aug. 15, 2006

(54) BETA-LACTAMASE INHIBITOR PRODRUG

(75) Inventors: Anthony Marfat, Mystic, CT (US); Dale G. McLeod, Ledyard, CT (US)

(73) Assignee: Pfizer Inc., New York, NY (US)

( * ) Notice: Subject to any disclaimer, the term of this patent is extended or adjusted under 35 U.S.C. 154(b) by 270 days.

(21) Appl. No.: 10/648,408

(22) Filed: Aug. 25, 2003

(65) Prior Publication Data

US 2004/0110740 A1    Jun. 10, 2004

Related U.S. Application Data

(60) Provisional application No. 60/405,640, filed on Aug. 23, 2002.

(51) Int. Cl.
*C07D 499/861*  (2006.01)
*A61K 31/43*    (2006.01)
*A61P 31/04*    (2006.01)

(52) U.S. Cl. .................................. 514/195; 540/310
(58) Field of Classification Search ................ 514/195; 540/310

See application file for complete search history.

(56) References Cited

U.S. PATENT DOCUMENTS

| | | | |
|---|---|---|---|
| 3,719,668 A | 3/1973 | Frederiksen et al. | 260/239.1 |
| 3,862,181 A | 1/1975 | Davis et al. | 260/243 C |
| 3,864,331 A | 2/1975 | Frederiksen et al. | 260/239.1 |
| 3,931,405 A | 1/1976 | Ekstrom et al. | 424/271 |
| 3,957,764 A | 5/1976 | Lund | 260/240 G |
| 4,287,181 A | 9/1981 | Kellogg | 424/114 |
| 4,397,783 A | 8/1983 | Kellogg et al. | 260/245.2 R |
| 4,406,887 A | 9/1983 | Gordon et al. | 424/114 |
| 4,428,935 A | 1/1984 | Myers | 424/114 |
| 4,432,970 A | 2/1984 | Kellogg | 424/114 |
| 4,521,533 A | 6/1985 | Hamanaka et al. | 514/80 |
| 4,540,689 A | 9/1985 | Muto et al. | 514/196 |
| 5,373,018 A | 12/1994 | Cugola et al. | 514/419 |
| 5,374,648 A | 12/1994 | Cugola et al. | 514/419 |
| 5,374,649 A | 12/1994 | Cugola et al. | 514/719 |
| 5,401,868 A | 3/1995 | Lund | 558/280 |
| 2005/0004093 A1 | 1/2005 | Marfat et al. | |

FOREIGN PATENT DOCUMENTS

| | | |
|---|---|---|
| EP | 0379132 | 7/1990 |
| GB | 1267936 | 3/1972 |
| GB | 1315566 | 5/1973 |
| GB | 1377573 | 12/1974 |
| GB | 1426717 | 3/1976 |
| GB | 2053220 | 2/1981 |
| GB | 2076812 | 12/1981 |
| JP | 58049387 | 3/1983 |
| JP | 3206038 | 3/1991 |

OTHER PUBLICATIONS

English, A. R., et al., *Orally Effective Acid Prodrugs of the β-Lactamase Inhibitor Sulbactam*, J. Med. Chem., vol. 33, pp. 344-347, (1990).
Patent Abstracts of Japan, vol. 0154, No. 74 (C-0809), (1991), Abstract for JP3206038.
English language abstract for EP0379132.
English language abstract for JP58049387.

*Primary Examiner*—Mark L. Berch
(74) *Attorney, Agent, or Firm*—Gregg C. Benson; Frank W. Forman

(57) ABSTRACT

Prodrugs of 6-β-hydroxymethylpenicillanic acid sulfone having the structure

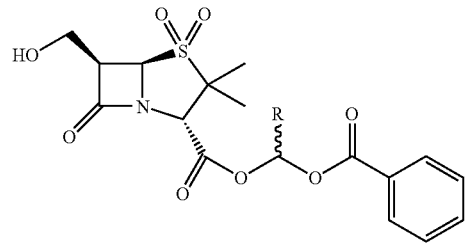

wherein R is H or methyl, and solvates thereof, are disclosed. Also disclosed are pharmaceutical compositions comprising a prodrug of the present invention or a solvate thereof, an optional beta-lactam antibiotic and a pharmaceutically acceptable excipient.

Further disclosed is a method for increasing the therapeutic effectiveness of a beta-lactam antibiotic in a mammal by administering an effective amount of a beta-lactam antibiotic and an effectiveness-increasing amount of a prodrug of the present invention, or a solvate thereof.

Additionally disclosed is a method for treating a bacterial infection in a mammal by administering a therapeutically effective amount of a pharmaceutical composition of the present invention to a mammal in need thereof.

13 Claims, No Drawings

BETA-LACTAMASE INHIBITOR PRODRUG

BACKGROUND OF THE INVENTION

Beta-lactam antibiotics, which generally are penicillins and cephalosporins, have been widely used in the treatment of infections, primarily bacterial, in mammals such as man. Certain micro-organisms are believed to be resistant to these antibiotics because they produce various beta-lactamase enzymes which attack the beta-lactam ring of the antibiotic thereby rendering the drug ineffective.

In U.S. Pat. No. 4,287,181, Kellogg disclosed that various 6β-hydroxyalkylpenicillanic acids, including 6-β-hydroxymethylpenicillanic acid sulfone which is the beta-lactamase inhibitor used in the present invention, are potent beta-lactamase inhibitors. U.K. Patent Application GB2053220A, Metzger et al. and U.K. Patent Application GB2076812, by Schneider et al., likewise disclosed that 6-β-hydroxymethyl-penicillanic acid sulfone is a beta-lactamase inhibitor. However, the beta-lactamase inhibitor 6-β-hydroxymethyl-penicillanic acid sulfone is very poorly absorbed in vivo in rodents during preclinical studies when administered orally.

Kellogg, Metzger et al. and Schneider et al. also disclosed ester prodrugs of 6-β-hydroxymethyl-penicillanic acid sulfone, which readily hydrolyze in vivo, during preclinical studies, and which demonstrated better absorption in rodents than did the free acid.

However, many of these ester prodrugs could only be synthesized as oils or as solids that had low melting points whose usefulness in pharmaceutical formulations is more limited than would be a solid prodrug with a melting point suitable for tableting, milling or purification.

Furthermore, these ester prodrugs were typically not highly absorbed when orally administered. Thus, higher drug dosages would be required to be administered orally, to obtain a therapeutically effective plasma level of the beta-lactamase inhibitor 6-β-hydroxy-methylpenicillanic acid sulfone, than would be required for a more highly absorbed prodrug. In addition, oral administration of the less absorbed prodrugs may result in an increase in the incidence and severity of diarrhea experienced by the recipient as the unabsorbed prodrug may hydrolyze in the gastro-intestinal tract, to form the active drug, and, with any residual amoxicillin, selectively kill essential components of the normal microbial flora. Further, it is desirable that the process, for producing the desired prodrug, be relatively inexpensive.

Therefore, there is a need for a crystalline prodrug of the beta-lactamase inhibitor 6-β-hydroxymethylpenicillanic acid sulfone which has a high oral bioavailability, and more preferably is crystalline with a suitable melting point.

SUMMARY OF THE INVENTION

The present invention relates to prodrugs of 6-β-hydroxymethylpenicillanic acid sulfone (also named 4-thia-1-azabicyclo[3.2.0]heptane-2-carboxylic acid, 6-(hydroxymethyl)-3,3-dimethyl-7-oxo-, 4,4-dioxide (2S, 5R, 6R)) having the structure

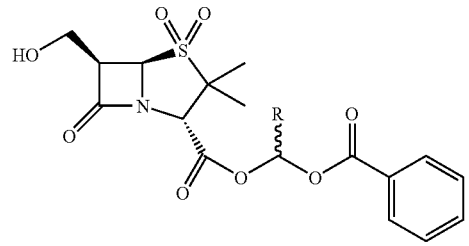

and solvates thereof, wherein R is H or methyl. The prodrugs of the present invention include 4-thia-1-azabicyclo[3.2.0] heptane-2-carboxylic acid, 6-(hydroxymethyl)-3,3-dimethyl-7-oxo-, -1-(benzoyloxy)-methyl ester, 4,4-dioxide (2S, 5R, 6R); 4-thia-1-azabicyclo[3.2.0]heptane-2-carboxylic acid, 6-(hydroxymethyl)-3,3-dimethyl-7-oxo-, -1-(benzoyloxy)-ethyl ester, 4,4-dioxide (2S, 5R, 6R); 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R); and 4-thia-1-azabicyclo[3.2.0] heptane-2-carboxylic acid, 6-(hydroxymethyl)-3,3-dimethyl-7-oxo-, (1S)-1-(benzoyloxy)ethyl ester, 4,4-dioxide (2S, 5R, 6R). The preferred prodrug of the present invention is 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R), which has the structure

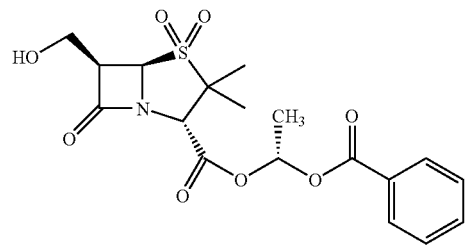

or a solvate thereof.

The present invention also relates to pharmaceutical compositions comprising a prodrug of the present invention or a solvate thereof, an optional beta-lactam antibiotic, and a pharmaceutically acceptable excipient. Preferably, the beta-lactam antibiotic is amoxicillin. It is also preferred that the prodrug, used in the pharmaceutical composition, is 4-thia-1-azabicyclo[3.2.0]heptane-2-carboxylic acid, 6-(hydroxymethyl)-3,3-dimethyl-7-oxo-, (1R)-1-(benzoyloxy) ethyl ester, 4,4-dioxide (2S, 5R, 6R) or a solvate thereof. It is more preferred that the pharmaceutical composition comprises 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R), or a solvate thereof, amoxicillin and a pharmaceutically acceptable excipient.

The present invention further relates to a method for increasing the therapeutic effectiveness of a beta-lactam antibiotic in a mammal comprising administering to said mammal an effective amount of a beta-lactam antibiotic and an effectiveness-increasing amount of a prodrug of the present invention, or a solvate thereof. Preferably, the beta-lactam antibiotic is amoxicillin. It is also preferred that the prodrug used is 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R) or a solvate thereof. It is more preferred that the prodrug is 4-thia-1-azabicyclo[3.2.0]heptane-2-carboxylic acid, 6-(hydroxymethyl)-3,3-dimethyl-7-oxo-, (1R)-1-(benzoyloxy) ethyl ester, 4,4-dioxide (2S, 5R, 6R), or a solvate thereof, and the beta-lactam antibiotic is amoxicillin. It is further preferred that the mammal is a human.

The present invention additionally relates to the treatment of a bacterial infection in a mammal by administering a therapeutically effective amount of a pharmaceutical composition of the present invention to a mammal in need thereof. Preferably, this pharmaceutical composition further comprises a beta-lactam antibiotic. More preferably, the beta-lactam antibiotic is amoxicillin. It is also preferred that the prodrug used is 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R) or a solvate thereof. It is more preferred that the prodrug is 4-thia-1-azabicyclo[3.2.0]heptane-2-carboxylic acid, 6-(hydroxymethyl)-3,3-dimethyl-7-oxo-, (1R)-1-(benzoyloxy) ethyl ester, 4,4-dioxide (2S, 5R, 6R), or a solvate thereof, and the beta-lactam antibiotic is amoxicillin. It is further preferred that the mammal is a human.

DETAILED DESCRIPTION

The terms used to describe the present invention have the following meanings herein.

The term "a" means at least one. Thus, for example, the phrase "a pharmaceutically acceptable excipient" means at least one pharmaceutically acceptable excipient.

The term "effective amount" means the amount of beta-lactam antibiotic which, when administered either alone, or in combination with a prodrug of the present invention, prevents the onset of, alleviates the symptoms of, stops the progression of, or eliminates a bacterial infection in a mammal.

The term "effectiveness-increasing amount" means that amount of prodrug which, when administered to a mammal and which subsequently hydrolyzes in vivo to form the beta-lactamase inhibitor of the present invention, increases the therapeutic effectiveness of a co-administered beta-lactam antibiotic.

The term "mammal" is an individual animal that is a member of the taxonomic class Mammalia. The class Mammalia includes, for example, humans, monkeys, chimpanzees, gorillas, cattle, swine, horses, sheep, dogs, cats, mice and rats.

In the present invention, the preferred mammal is a human, male or female.

The term excipient, as used herein, means any component of a pharmaceutical formulation other than the prodrug or optional beta-lactamase antibiotic.

The term "pharmaceutically acceptable excipient" means that said excipient must be compatible with other ingredients of the composition, and not deleterious to the recipient thereof. Pharmaceutical compositions of the present invention are prepared by procedures known in the art using well known and readily available ingredients.

The prodrugs of the present invention include 4-thia-1-azabicyclo[3.2.0]heptane-2-carboxylic acid, 6-(hydroxymethyl)-3,3-dimethyl-7-oxo-, -1-(benzoyloxy)-methyl ester, 4,4-dioxide (2S, 5R, 6R) which is described in Example 3, and 4-thia-1-azabicyclo[3.2.0]heptane-2-carboxylic acid, 6-(hydroxymethyl)-3,3-dimethyl-7-oxo-, -1-(benzoyloxy) ethyl ester, 4,4-dioxide (2S, 5R, 6R) which is described in Example 4.

The prodrugs of the present invention, as further described in Example 9, are stable in the upper GI tract but, after absorption, readily hydrolyze in vivo to form 6-β-hydroxymethylpenicillanic acid sulfone (hereinafter know as "6-β-HMPAS") which is a beta-lactamase inhibitor that increases the effectiveness of beta-lactam antibiotics against beta-lactamase-producing bacteria. This beta-lactamase inhibition generally preserves the antibacterial potency of a co-administered beta-lactam antibiotic against beta-lactamase (+) strains.

As the prodrugs of the present invention hydrolyze in vivo and form the free acid beta-lactamase inhibitor 6-β-HMPAS, these prodrugs are useful in that, when administered to a mammal, the effectiveness of a co-administered beta-lactam antibiotic against beta-lactamase producing bacteria will be enhanced.

Prodrugs of this invention may be used, in combination therapy with beta-lactam antibiotics, to treat infections of, for example, the respiratory tract, the urinary tract and soft tissues in humans. Compositions of this invention may also be used to treat infections in other mammals, such as mastitis in cattle.

Bacterial infections amenable to treatment by the prodrug, pharmaceutical composition and method of the present invention include, but are not limited to, upper respiratory diseases including community acquired pneumoniae (CAP), acute exacerbations of chronic bronchitis (AECB) and acute bacterial sinusitis (ABS), caused by respiratory pathogens, such as *Haemophilus influenzae* and *Moraxella catarrhalis* including antibiotic resistant isolates.

Further, bacterial infections amenable to treatment, by pharmaceutical compositions of the present invention which contain an antibiotic, include, but are not limited to, pediatric otitis media, sinusitis, pneumonia and acute exacerbations of bronchitis in adults caused by *H. influenzae* or *Streptococcus pneumoniae*, including Drug Resistant *S. pneumoniae* (DRSP) such as Penicillin Resistant *S. pneumoniae*.

Additional, bacterial infections amenable to treatment, by pharmaceutical compositions of the present invention which contain an antibiotic, include, but are not limited to, soft tissue infections caused by *E. Coli, Klebsiella pneumoniae, Enterobacter* spp. and all other members of the family Enterobacteriaceae.

Other infections amenable to treatment, by pharmaceutical compositions of the present invention which contain an antibiotic, include, but are not limited to, those caused by beta-lactamase producing methicillin susceptible staphylococci and beta-lactamase producing anaerobes.

As the prodrugs of the present invention contain more than one chiral center, they exist in different optically active diasteriomeric forms. More specifically, the preferred prodrugs of the present invention contain a chiral center at the 1-ethyl location. The present invention includes both 1R and 1S diastereomers of 4-thia-1-azabicyclo[3.2.0]heptane-2-carboxylic acid, 6-(hydroxymethyl)-3,3-dimethyl-7-oxo-, -1-(benzoyloxy)ethyl ester, 4,4-dioxide (2S, 5R, 6R), and also includes, and mixtures of these diastereomers, such as racemic mixtures. These diastereomeric forms, a mixture thereof, and their respective syntheses are further described herein in the following Examples 4–6.

Even more preferably, the prodrug of the present invention comprises the 1R diastereomer of 4-thia-1-azabicyclo[3.2.0]-heptane-2-carboxylic acid, 6-(hydroxymethyl)-3,3- dimethyl-7-oxo-, -1-(benzoyloxy)ethyl ester, 4,4-dioxide (2S, 5R, 6R) as is described in Example 5.

The prodrugs of the present invention may exhibit polymorphism. Polymorphs of prodrugs form part of this invention and may be prepared by crystallization of a prodrug of the present invention under different conditions. For example, using different solvents or different solvent mixtures for recrystallization; crystallization at different temperatures; various modes of cooling ranging from very fast to very slow cooling during crystallization. Polymorphs may also be obtained by heating or melting a prodrug followed by gradual or fast cooling. The presence of polymorphs may be determined by solid probe nmr spectroscopy, ir spectroscopy, differential scanning calorimetry, powder X-ray diffraction or other such techniques.

The prodrugs of the present invention may also exist in the form of solvates, for example, hydrates, ethanolate, n-proponalate, iso-propanolate, 1-butanolate, 2-butanolate and solvates of other physiologiaclly acceptable solvents, such as the Class 3 solvents described in the *International Conference on Harmonization (ICH), Guidance for Industry, Q3C Impurities: Residual Solvents* (1997). The present invention includes each solvate and mixtures thereof.

For a prodrug, the minimum amount of prodrug administered is that amount which will increase the effectiveness of a co-administered beta-lactam antibiotic. The maximum amount of prodrug administered is that amount, which either alone or in combination with the beta-lactam antibiotic, is toxicologically acceptable.

Typically, for adults and children weighing at least 40 kg, the daily dosage amount of prodrug is between about 200 mg to about 1 g or more. For children weighing less than 40 kg, the daily dosage amount of prodrug is between about 7 mg/kg/day to about 20 mg/kg/day or more. However, these figures are illustrative only, and, in some cases, it may be necessary to use dosages outside these limits.

A daily dosage of the prodrug of the present invention can be administered from 1 to 4 times daily in equal doses.

In the treatment of a bacterial infection, a prodrug of the present invention is co-administered with a beta-lactam antibiotic. The prodrug and the beta-lactam antibiotic may be administered concurrently or sequentially. Further, the prodrug and antibiotic may be contained in separate pharmaceutical compositions or in a single pharmaceutical composition.

Typical beta-lactam antibiotics, with which the prodrug of the present invention is co-administered, are beta-lactam antibiotics which are sensitive to enzymatic degradation and inactivation by various beta-lactamase enzymes. Examples of such beta-lactamase sensitive antibiotics include, but are not limited to, penicillins such as natural penicillins, amoxicillin and ampicillin; cephalosporins such as cefadroxil, cefazolin, cephalexin, cephalothin, cephapirin, cephradine, cefaclor, cefamandole, cefoicid, ceforanide, cefprozil, cefuroxime, cefdinir, cefoperazone, cefotaxime, cefpodoxime, ceftazidime, ceftibuten, ceftizoxime, ceftriaxone and cefepime; and monobactams such as aztreonam.

Typically, when contained together in a pharmaceutical composition, the weight ratio of beta-lactam antibiotic to prodrug is between about 15:1 to about 1:1.

Preferably, a prodrug of the present invention is co-administered with amoxicillin. More preferably, amoxicillin is co-administered with the prodrug 4-thia-1-azabicyclo [3.2.0]-heptane-2-carboxylic acid, 6-(hydroxymethyl)-3,3-dimethyl-7-oxo-, (1R)-1-(benzoyloxy)ethyl ester, 4,4-dioxide (2S, 5R, 6R).

The term "amoxicillin" as used herein shall mean amoxicillin or an alkaline salt, or hydrate thereof such as, in particular, amoxicillin trihydrate or (crystallized) sodium amoxicillin. Unless otherwise indicated, weights of amoxicillin refer to the equivalent weight of the corresponding free acid. In addition, it will be appreciated that in practice, weights of amoxicillin to be incorporated into a formulation will be further adjusted, in accord with conventional practice, to take account of the potency of the amoxicillin.

Typically, an effective amount of amoxicillin, for adults and children weighing at least 40 kg, is a daily dosage level of about 250 mg to about 5 g. For children weighing less than 40 kg, an effectiveness-increasing amount of amoxicillin is a daily dosage level of about 20 mg/kg/day to about 150 mg/kg/day. However, these figures are illustrative only, and, in some cases, it may be necessary to use dosages outside these limits.

A daily dosage of amoxicillin can be administered from 1 to 4 times daily in equal doses in the form of immediate, modified or delayed (or slow) release compositions. Formulations of immediate, modified and delayed (slow) release pharmaceutical compositions containing amoxicillin, which are suitable for the pharmaceutical composition of the present invention, and the preparation thereof, are described in U.S. Pat. Nos. 4,537,887, issued to Rooke et al., U.S. Pat. No. 6,051,255, issued to Conley et al., U.S. Pat. No. 6,218,380, issued to Cole et al., U.S. Pat. No. 6,051,255, issued to Conley et al.; U.S. patent application Ser. No. 09/911,905, by Conley et al.; and International Application Number PCT/IB01/01899, by Conley et al. The teachings of U.S. Pat. Nos. 4,537,887, 6,051,255, 6,218,380, 6,051,255, U.S. Ser. No. 09/911,905 and International Application Number PCT/IB01/01899 regarding immediate, modified and delayed release amoxicillin formulations are incorporated herein by reference.

In these compositions, the exact amount of prodrug and amoxicillin will depend to some extent on the microorganism which is being treated.

As will be appreciated by one skilled in the art, some of the beta-lactam compounds are effective when administered orally or parenterally, while others are effective only when administered parenterally. When a prodrug of the present invention is combined with a parenterally administered beta-lactam antibiotic, a pharmaceutical suitable for which is effective only on parenteral administration, a combination formulation suitable for parenteral use will be employed. When the prodrug is to be combined with a beta-lactam antibiotic which is effective orally or parenterally, combinations suitable for either oral or parenteral administration can be prepared. Additionally, it is possible to administer preparations of the prodrug orally, while administering a further beta-lactam antibiotic parenterally; and it is also possible to administer preparations of the prodrug parenterally, while administering the further beta-lactam antibiotic orally.

A pharmaceutical composition, of the present invention, comprises a prodrug of the present invention and a pharmaceutically acceptable excipient.

Optionally, the pharmaceutical composition further comprises a beta-lactam antibiotic. It is preferred that the antibiotic is amoxicillin. It is also preferred that the prodrug is 4-thia-1-azabicyclo-[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R). It is more preferred that the pharmaceutical composition comprises 4-thia-1-azabicyclo[3.2.0]heptane-2-carboxylic acid, 6-(hydroxymethyl)-3,3-dimethyl-7-oxo-, (1R)-1-(benzoyloxy)

ethyl ester, 4,4-dioxide (2S, 5R, 6R), amoxicillin and a pharmaceutically acceptable excipient.

Typically, excipients, are as known in the art, and include, but are not limited to binders, fillers and extenders, carriers or vehicles, diluents, disintegrants, lubricants, glidants, stabilizers, buffers, bulking or thichening agents, emulsifiers, suspending agents, flavors, sweeteners, and pigments.

Examples of excipients that are suitable for such pharmaceutical compositions include: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents.

Suitable examples of methods of preparing pharmaceutical compositions are provided in Remington's Pharmaceutical Sciences, Mack Publishing Company, Easton, Pa., 18th Edition (1990).

In preparing a pharmaceutical composition of the present invention, the prodrug, and optional beta-lactam antibiotic, are usually mixed with an excipient, diluted by an excipient or enclosed within a carrier that can be in the form of a capsule, sachet, or other container. When the excipient serves as a diluent, it can be a solid, semi-solid, or liquid material that acts as a vehicle, carrier or medium for the active ingredient.

The pharmaceutical composition can be administered orally or parenterally, i.e. intramuscularly, subcutaneously, intravenously or intraperitoneally. The carrier is chosen on the basis of the intended mode of administration. For example, when considering the oral mode of administration, a pharmaceutical composition of this invention can be used in the form of tablets including chewable tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredients, as well as the dosage contemplated. However, pharmaceutical compositions containing a beta-lactam antibiotic and a prodrug of the present invention will preferably contain from about 20% to about 95% of active ingredients. In the case of tablets for oral use, carriers which are commonly used include, for example, lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents include, for example, are lactose and high molecular weight polyethylene glycols. When aqueous solutions or suspensions are required for oral use, the active ingredient may be combined with emulsifying and suspending agents. If desired, certain sweetening and/or flavoring agents can be added. For parenteral administration, sterile solutions of the active ingredients are usually prepared, and the pH of the solutions is suitably adjusted and buffered. For intravenous use, the total concentration of solutes should be controlled to render the preparation isotonic.

The formulations of the invention may be made up into solid dosage forms for oral administration by a method conventional to the art of pharmaceutical technology, e.g. tablets or powder or granular products for reconstitution into a suspension or solution.

Suitable ingredients and suitable methods for making such tablets are disclosed in, for example, International Applications WO 92/19227 and WO 95/28927 the teachings of which, regarding tablet ingredients and methods for making tablets, are incorporated herein by reference. Powder or granular formulations, such as pediatric suspension formulations, may be manufactured using techniques which are generally conventional in the field of manufacture of pharmaceutical formulations and in the manufacture of dry formulations for reconstitution into such suspensions. For example a suitable technique is that of mixing dry powdered or granulated ingredients for loading into a suitable container.

For pediatric dosing, the formulations of the invention are preferably made up into a sweet flavored aqueous syrup formulation of generally conventional formulation (except for its novel amoxicillin:prodrug ratio and intended use) containing a suitable weight of the amoxicillin and prodrug in a unit dose volume, e.g. 5 ml or 2.5 ml preferably as a syrup. A pediatric formulation may therefore comprise a bulk of a solution or suspension, e.g. a syrup, or granules or powder which can be made up into such a solution or suspension, at a concentration of solution or suspension which contains such a dose in such a volume. Suitable such formulations are described in International application no PCT EP96/01881 (SmithKline Beecham). The formulation of this invention will normally, in addition to its active materials amoxicillin and prodrug, also include excipients which are standard in the field of formulations for oral dosing and used in generally standard proportions, and at generally standard particle sizes and grades etc.

In the case of pediatric oral suspensions, these excipients may comprise suspending aids, glidants (to aid filling), diluents, bulking agent, flavors, sweeteners, and stabilizers.

Suitable excipients for use include, for example, xantham gum (suspension aid), colloidal silica (glidant), succinic acid (stabilizer), aspartame (sweetener), hydroxypropylmethylcellulose (suspension aid) and silicon dioxide (diluent for prodrug and bulking agent). Flavors may comprise common flavors such as bubble gum, orange, banana, raspberry, grape and golden syrup, or mixtures thereof, to suit local requirements.

The pharmaceutical composition of the present invention may, for example, be provided in solid unit dose forms embodying suitable quantities for the administration of such a daily dose. For example a unit dosage form may be tablets, or sachets containing granules or powders for reconstitution, one or two of which are to be taken 1–4 times daily. Alternatively a unit dose may be provided as a bulk of solid or solution or suspension, e.g. as a syrup for pediatric administration, together with a suitable measuring device of known type to facilitate administration of a suitable unit dose quantity of the formulation. A suitable unit dose quantity is one which enables the administration of the above-mentioned daily dosage quantity divided 1–4 doses.

Yet another embodiment of this invention is a kit, for achieving an antibacterial therapeutic effect in a mammal, comprising (1) a pharmaceutical composition, which comprises a prodrug of the present invention and, optionally, a beta-lactam antibiotic, and (2) directions for the administration of the pharmaceutical composition in a manner to achieve the desired therapeutic effect.

The present invention will be further illustrated by means of the following examples. It is to be understood, however, that the invention is not meant to be limited to the details described therein.

EXAMPLE 1

Preparation and Enantiomeric Separation of (R/S) Benzoic acid 1-chloro-ethyl ester

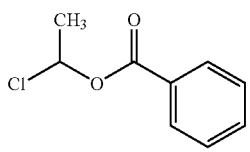

(R/S)-Benzoic acid 1-chloro-ethyl ester, shown above, was prepared as follows.

To a stirred solution of 122 g (862 mmol.) benzoyl chloride (Aldrich), under a nitrogen atmosphere in a 3-neck round bottom flask, was added 2.35 g (17.2 mmol.) anhydrous zinc chloride (Aldrich). The reaction mixture was stirred for 15 minutes at room temperature and then cooled to −15° C. using an ethylene glycol/$CO_2$ bath. To this mixture was added slowly 37.9 g (862 mmol.) acetaldehyde (Aldrich) while maintaining an internal temperature below 0° C. After addition was completed, the reaction mixture was allowed to warm to room temperature. 400 mL water and 400 mL $CH_2Cl_2$ were added and then the layers were separated. The organic layer was separated and washed with saturated $NaHCO_3$, water, brine, dried over $MgSO_4$ filtered and concentrated in vacuo. Chromatography on silica gel eluting with 1.75% ethyl acetate/98.25% hexanes afforded 55.4 g of a yellow oil. $^1$H-NMR ($CDCl_3$, 400 MHz): 8.08 (d, 2H, J=7.5 Hz), 7.61 (t, 1H, J=7.5 Hz), 7.47 (t, 2H, J=7.5 Hz), 6.80 (q, 1H, J=6 Hz), 1.93 (d, 3H, J=6 Hz).

(R)-Benzoic acid 1-chloro-ethyl ester, shown below, was isolated by the chiral separation of (+/−)-benzoic acid 1-chloro-ethyl ester using a 10 cm by 50 cm Chiralcel OJ column eluting with heptane/IPA (98/2) and with a flow rate of 250 mL/min. The enantiomer collected eluted second with an analytical purity retention time of 7.123 min.

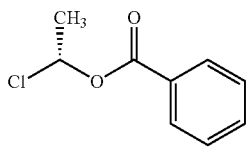

$^1$H-NMR ($CDCl_3$, 400 MHz): 8.08 (d, 2H, J=7.5 Hz), 7.61 (t, 1H, J=7.5 Hz), 7.47 (t, 2H, J=7.5 Hz), 6.80 (q, 1H, J=6 Hz), 1.93 (d, 3H, J=6 Hz). $[\alpha_d]$=−140° (C+0.0315, $CHCl_3$).

(S)-Benzoic acid 1-chloro-ethyl ester, shown below, was isolated by the chiral separation of (+/−)-benzoic acid 1-chloro-ethyl ester using a 10 cm by 50 cm Chiralcel OJ column eluting with heptane/IPA (98/2) and with a flow rate of 250 mL/min. The enantiomer collected eluted first with an analytical purity retention time of 5.807 min.

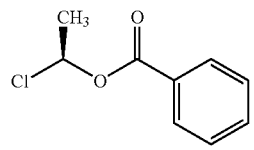

H-NMR ($CDCl_3$, 400 MHz): 8.08 (d, 2H, J=7.5 Hz), 7.61 (t, 1H, J=7.5 Hz), 7.47 (t, 2H, J=7.5 Hz), 6.80 (q, 1H, J=6 Hz), 1.93 (d, 3H, J=6 Hz). $[\alpha_d]$=+130° (C+0.0345, $CHCl_3$).

EXAMPLE 2

Preparation of 4-Thia-1-azabicyclo[3.2.0]heptane-2-carboxylic acid, 6-(hydroxymethyl)-3,3-dimethyl-7-oxo-4,4-dioxide, monosodium salt, (2S, 5R, 6R)

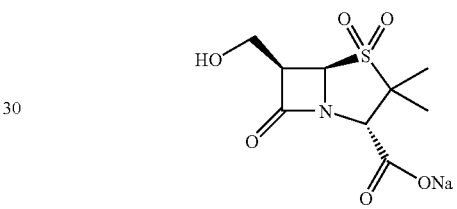

4-Thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R), shown above, (hereinafter "Na-HMPAS") was prepared by the following four-step process.

Step 1—Preparation of sodium 6,6-dibromopenicillanate sulfone

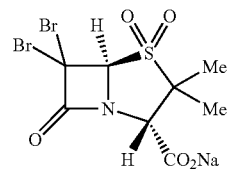

Ethyl acetate (15.8 L) was added to 6,6-dibromopenicillanic acid sulfone (2500 g) and heated to 50° C. Sodium ethyl hexanoate (1044 g) and ethyl acetate (5.0 L) were stirred to form a solution then added to the 6,6-dibromopenicillanic acid sulfone solution over a 60 minute period. The reaction mixture was allowed to cool to ambient temperature and the resulting solids granulated for a period of 1 hour. The product was collected by filtration and washed with ethyl acetate to give 2197 g (83%) of the sodium 6,6-dibromopenicillanate sulfone. M.P. 186–187° C. $^1$HNMR ($D_2O$) δ 1.30 (s, 3H), 1.45 (s, 3H), 4.29 (s, 1H), 5.54 (s, 1H).

Step 2—Preparation of benzyl 6,6-dibromopenicillanate sulfone

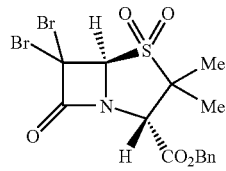

Dimethylformamide (5.7 L) and the sodium 6,6-dibromopenicillanate sulfone (3820 g) were combined and the mixture was stirred for a few minutes until all of the solids dissolved. To this mixture benzyl bromide (1400 g) was added over a 1 hour period. The reaction mixture was then stirred overnight at ambient temperature. Water (4.5 L) and ethyl acetate (15.0 L) were added to quench the reaction. The aqueous phase was washed with ethyl acetate (2×600 mL) and the combined organic phases were washed sequentially with a saturated aqueous sodium bicarbonate solution (2×1 L) and an aqueous sodium chloride solution (2×1 L). The organic layer was dried over magnesium sulfate and concentrated to give 3566 g (90%) of the desired benzyl 6,6-dibromopenicillanate sulfone as crystals. M.P. 146–147° C. $^1$HNMR (CDCl$_3$) δ 1.2 (s, 3H), 1.5 (s, 3H), 4.5 (s, 1H), 4.9 (s, 1H), 5.16 (d, 1H, J=12 Hz), 5.29 (d, 1H, J=12 Hz), 7.35–7.40 (m, 5H).

Step 3—Preparation of benzyl 6-β-hydroxymethyl-6-α-bromopenicillanate sulfone

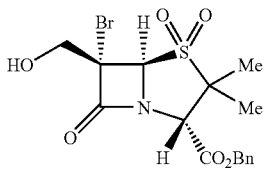

In a round bottom flask, paraformaldehyde was heated under a nitrogen sweep to 160–180° C. to express excess water. In a separate round bottom flask tetrahydrofuran (8.0 L) and benzyl 6,6-dibromopenicillanate sulfone (1000 g) were combined and stirred until all of the solids had dissolved. The solution was cooled to −78° C. and 3M methylmagnesium chloride in THF (720 mL) was added slowly to the solution while maintaining the temperature less than −70° C. The reaction mixture was stirred for 1 hour. At this time, formaldehyde gas expressed from the first round bottom flask was blown over the surface of the chilled reaction mixture using a stream of nitrogen. This formaldehyde gas was expressed over the reaction mixture for approximately 6 hours while maintaining cooling and vigorous stirring of the chill reaction flask. Upon reaction completion determined by TLC (80:20 hexanes:ethyl acetate), the reaction was quenched at −78° C. with a solution of acetic acid (132 mL) in THF (400 ML). The reaction mixture was allowed to warm to ambient temperature then the reaction mixture was filtered through Supercel. The filtrate was concentrated to an oil (~1000 g). The oil was then transferred to a large reaction vessel and ethyl acetate (5.0 L)/water (2.5 L) added. The mixture was stirred, then separated. The aqueous layer was washed with ethyl acetate (2×500 mL). The combined organic layers were sequentially washed with 1N hydrochloric acid (3.0 L), water (3×3.0 L), and saturated aqueous sodium chloride solution (3×3.0 L). The organic layer was dried with magnesium sulfate, filtered through Supercel®, a calcined filter aid (Celite Corporation, Lompoc, Calif.), concentrated and stored in a refrigerator. The resulting oil was chromatographed through silica gel (1 Kg per 500 g of product oil), and eluted with 9:1 hexane/ethyl acetate (20.0 L) to remove impurities then 4:1 hexane/ethyl acetate (4.0–8.0 L) and finally 3:2 hexane/ethyl acetate (as needed) until the benzyl 6-β-hydroxymethyl-6-α-bromopenicillanate sulfone was removed. Yield 205.5 g (23%). M.P. 120–121° C. (CDCl$_3$) $^1$HNMR δ 1.28 (s, 3H), 1.57 (s, 3H), 4.09 (d, 1H, J=16 Hz), 4.54 (s, 1H), 4.62 (d, 1H, J=16 Hz), 4.82 (s, 1H), 5.18 (d, 1H, J=16 Hz), 5.32 (d, 1H, J=16 Hz), 7.36–7.42 (m, 5H).

Step 4—Preparation of 4-Thia-1-azabicyclo[3,2,0] heptane-2-carboxylic acid, 6-(hydroxymethyl)-3,3-dimethyl-7-oxo-, 4,4-dioxide, monosodium salt, (2S, 5R, 6R)

Water (163 mL), ethyl acetate (2000 mL), benzyl 6-β-hydroxymethyl-6-α-bromopenicillanate sulfone (180 g), triethylamine (90.0 g) and 5% palladium on carbon (45 g) were combined and hydrogenated at 50 psi at ambient temperature for approximately 2 hours. A TLC of the reaction mixture showed the reaction was not complete so additional catalyst (15 g) was added and the mixture was hydrogenated for one hour. Once the reaction was complete, the reaction was quenched with a mixture of sulfuric acid (112.5 g) and water (270 mL). The reaction mixture was filtered to remove catalyst, and washed with EtOAc (450 mL). The aqueous layer was washed with EtOAc (3×750 mL). The organic phases were combined and dried with calcium chloride to a water content of less than 1%. The calcium chloride was then filtered out and the ethyl acetate was reduced to ½ its volume. Fresh ethyl acetate was then back added to the solution and the water content of the solution was now 0.09%. Sodium ethyl hexanoate (59 g) and EtOAc (450 mL) were combined and added slowly to organic phase at ambient temperature. The mixture was then allowed to granulate for a period of 30 to 45 minutes. The resulting solids were filtered, washed with EtOAc (500 mL) and dried to give 79.0 g (66%) of sodium 6-β-hydroxymethylpenicillanate sulfone. The solids were further purified via a recrystallized from 2-propanol/water. M.P. 246–245° C. $^1$HNMR (D$_2$O) δ 1.23 (s, 3H), 1.39 (s, 3H), 3.82–3.89 (m, 1H), 3.97–4.10 (m, 3H), 4.85 (s, 1H)

Alternate Step 4—Preparation of 4-Thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R)

Benzyl 6-β-hydroxymethyl-6-α-bromopenicillanate sulfone (1143 g) was placed in a large reaction vessel. Benzene (6.2 L) and tributyltin hydride (770 mL) were added and the reaction mixture heated to reflux temperature for 2–3 hours. The reaction was monitored by TLC, solvent=1:1 hexane/Ethyl acetate.

Upon reaction completion the mixture was concentrated to an oil to remove the benzene. The oil was washed with hexane at ambient temperature, until all the residual tin byproducts were removed. The material was reheated to reflux; ethyl acetate (EtOAc) was added to transfer material to single necked flask and concentrated. The material was washed with hexane (3×) and the product layer dried under reduced pressure.

Half of the oil (549 g) was chromatographed over silica gel (1 Kg), with enough methylene chloride to get oil into solution, eluting with 7:3 hexane/EtOAc going to 3:2 hexane/EtOAc. The product fractions were combined and concentrated.

The oil (~540 g) was placed in an autoclave. Tetrahydrofuran (1.9 L), 10% palladium on carbon and water (300 mL) were added, and the reaction mixture hydrogenated at 50 psi, at a temperature of 30° C., for approximately 1 hour. Upon reaction completion the reaction mixture was filtered through celite, to remove catalyst.

The filtrate was concentrated and diluted with EtOAc (3.0 L). The aqueous layer was washed with EtOAc (1.0 L). The combined organic layers were dried with calcium chloride, and concentrated to half volume. EtOAc (2.5 L) was added followed dropwise by a solution of sodium ethyl hexanoate (SEH, 250 g) and EtOAc (1.05 L). The resulting solids were removed by filtration and dried in a vacuum oven.

To the resulting solids, water (6–800 mL) was added and the pH adjusted to between 0.5 and 1.0 with 4M sulfuric acid. The product was extracted with EtOAc (5×1.0 L). The combined organic phases were dried with calcium chloride and filtered through a sparkle filter. The filtrate was reduced to half volume and a solution of SEH (115.3 g) and EtOAc (500 mL0 added. The mixture was allowed to granulate. The resulting solids were filtered and washed with EtOAc to give desired product.

EXAMPLE 3

Prodrug 1: 4-Thia-1-azabicyclo[3.2.0]heptane-2-carboxylic acid, 6-(hydroxymethyl)-3,3-dimethyl-7-oxo-, (benzoyloxy)methyl ester, 4,4-dioxide (2S, 5R, 6R)

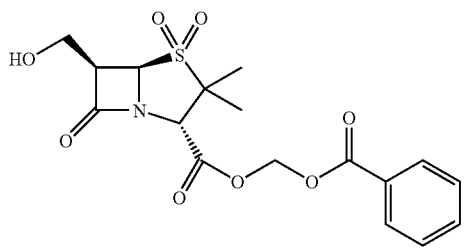

Prodrug 1, shown above, was prepared as follows.

To a stirred solution of 3.13 g (18.4 mmol.) chloromethyl benzoate (Narchem) in 200 mL acetone was added 13.8 g (92.1 mmol.) sodium iodide (Aldrich). The resulting mixture was stirred at room temperature overnight. To this solution was added 3.5 g (12.3 mmol.) 4-thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R). The reaction mixture was stirred overnight at room temperature. The reaction mixture was then concentrated in vacuo. Subsequently, 200 mL water and 200 mL ethyl acetate were added and the organic layer was separated and washed with brine, dried over $Na_2SO_4$, filtered and concentrated in vacuo. Chromatography on silica gel eluting with 1:1 ethyl acetate/hexanes afforded 8.62 g of an oil. The oil was then recrystallized from ethyl acetate/hexanes yielding 5.5 g of crystalline solid. The mother liquor still contained desired compound. Melting point=102° C. $^1$H-NMR (DMSO): 7.97 (d, 2H, J=7.5 Hz), 7.70 (t, 1H, J=7.5 Hz), 7.56 (t, 2H, J=7.5 Hz), 6.12 (d, 1H, J=6 Hz), 5.99 (d, 1H, J=6 Hz), 5.19 (d, 1H, J=5 Hz), 5.17 (m, OH), 4.62 (s, 1H), 4.20 (m, 1H), 4.03 (m, 1H), 3.73 (m, 1H), 1.41 (s, 3H), 1.28 (s, 3H).

EXAMPLE 4

Prodrug 2: 4-Thia-1-azabicyclo[3.2.0]heptane-2-carboxylic acid, 6-(hydroxymethyl)-3,3-dimethyl-7-oxo-, -1-(benzoyloxy)ethyl ester, 4,4-dioxide (2S, 5R, 6R)

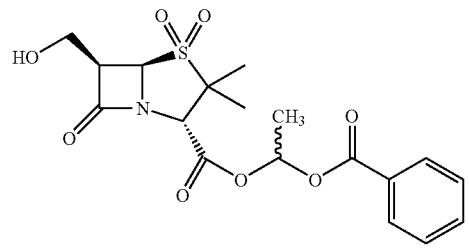

Prodrug 2, shown above, was prepared as follows.

To a stirred solution of 2.5 g (8.77 mmol.) 4-thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R) in 20 mL DMF was added 2.1 g (11.4 mmol.) (+/−)-benzoic acid 1-chloro-ethyl ester. The resulting mixture was then heated to 35° C. for 3 days. 40 mL water and 100 mL ethyl acetate were added and the layers were separated. The aqueous layer was extracted with ethyl acetate. The combined organic layers were washed with water, brine, dried over $Na_2SO_4$, filtered and concentrated in vacuo. Chromatography on silica gel eluting with 1 L of 20% ethyl acetate/80% hexanes followed by 1 L 1:1 ethyl acetate/hexanes afforded 1.2 g of an oil that was recrystallized using ethyl acetate/hexanes affording 1 g of white crystalline solid (mixture of 2 diastereomers). Melting point=133–135° C. $^1$H-NMR (d-DMSO, 400 MHz): 7.96 (d, 2H, J=7.5 Hz), 7.71 (t, 1H, J=7.5 Hz), 7.55 (t, 2H, J=7.5 Hz), 7.07 (q, 0.5H, J=5.4 Hz), 7.03 (q, 0.5H, J=5.4 Hz), 5.19 (d, 1H, J=5 Hz), 5.15 (m, OH), 4.54 (s, 0.5H), 4.53 (s, 0.5H), 4.19 (m, 1H), 4.01 (m, 1H), 3.73 (m, 1H), 1.62 (d, 1.5H, J=5.4 Hz), 1.61 (d, 1.5H, J=5.4 Hz), 1.44 (s, 1.5H) 1.38 (m, 4.5H).

EXAMPLE 5

Prodrug 3: 4-Thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide (2S, 5R, 6R)

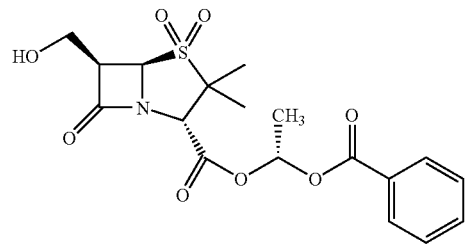

Prodrug 3, shown above, was prepared by the method of Example 4 by substituting (S)-Benzoic acid 1-chloro-ethyl ester and only heating to 30° C. Melting Point=154° C. $^1$H NMR (d-DMSO, 400 MHz): 7.96 (d, J=7.5 Hz, 2H), 7.71 (t, J=7.5 Hz, 1H), 7.55 (t, J=7.5 Hz, 2H), 7.03 (q, J=5.4 Hz, 1H), 5.19 (d, J=5 Hz, 1H), 5.15 (m, OH), 4.53 (s, 1H), 4.18 (m, 1H), 4.02 (m, 1H), 3.72 (m, 1H), 1.61 (d, J=5.4 Hz, 3H), 1.39 (s, 3H), 1.37 (s, 3H). [α]$_D$=+119 (C=0.0121, CHCl$_3$)

Prodrug 3 was also prepared by the following alternative route. 52.03 g (182.4 mmol.) of 4-thia-1-azabicyclo[3,2,0] heptane-2-carboxylic acid, 6-(hydroxymethyl)-3,3-dimethyl-7-oxo-, 4,4-dioxide, monosodium salt, (2S, 5R, 6R), 61.50 g (181.1 mmol.) of tetrabutylammonium hydrogen sulfate, and 15.44 g (183.2 mmol.) of sodium hydrogen carbonate were combined at 20° C. To this was added 400 mL dichloromethane while maintaining a temperature of 20° C. Next 100 mL of water was added. The resulting mixture was stirred at 20° C. for 30 minutes. Organic layer was separated and dried over sodium sulfate, filter and concentrated in vacuo. To the resulting residue was added 169.4 g (917.6 mmol.) (S)-Benzoic acid 1-chloro-ethyl ester followed by 160 mL acetone. The resulting solution was then stirred for 3 days at room temperature. Reaction was concentrated in vacuo and chromatographed on silica gel using 40–50% ethyl acetate/hexanes as eluent. The resulting product was crystallized from ethanol followed by recrystallization from ethyl acetate/hexanes. Filtration and drying in vacuo yielded 85.9 g of white crystalline product.

EXAMPLE 6

Prodrug 4: 4-Thia-1-azabicyclo[3.2.0]heptane-2-carboxylic acid, 6-(hydroxymethyl)-3,3-dimethyl-7-oxo-, (1S)-1-(benzoyloxy)ethyl ester, 4,4-dioxide (2S, 5R, 6R)

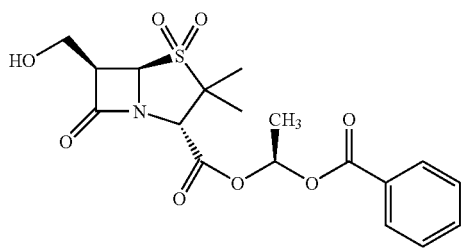

Prodrug 4, shown above, was prepared by the method of Example 4 by substituting (R)-benzoic acid 1-chloro-ethyl ester and only heating to 30° C. $^1$H-NMR (d-DMSO, 400 MHz): 7.96 (d, 2H, J=7.5 Hz), 7.71 (t, 1H, J=7.5 Hz), 7.55 (t, 2H, J=7.5 Hz), 7.07 (q, 1H, J=5.4 Hz), 5.19 (d, 1H, J=5 Hz), 5.15 (m, OH), 4.54 (s, 1H), 4.18 (m, 1H), 4.01 (m, 1H), 3.72 (m, 1H), 1.62 (d, 3H, J=5.4 Hz), 1.44 (s, 3H) 1.35 (s, 3H). MS (m/z): 410 (M$^-$ −1, 100).

EXAMPLE 7

Preparation of Carbonic Acids For Synthesizing Comparison Prodrugs of 4-thia-1-azabicyclo[3.2.0] heptane-2-carboxylic acid, 6-(hydroxymethyl)-3,3-dimethyl-7-oxo-, 4,4-dioxide (2S,5R,6R)

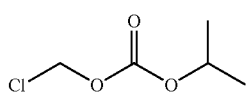

Carbonic acid chloromethyl ester isopropyl ester, shown above, was prepared as follows. To a stirred solution of 10 grams (75.2 mmol.) chloromethyl chloroformate (Fluka) in 100 mL dichloromethane at 0° C. was added 5.8 mL (76 mmol.) isopropyl alcohol followed by 11.93 g (97.8 mmol.) dimethyl amino pyridine (Fluka) The resulting reaction mixture was then allowed to warm to room temperature and stir overnight. The reaction mixture is then diluted with water. The layers were then separated. The organic layer was washed with brine, dried over MgSO$_4$ filtered and concentrated in vacuo yielding 6 grams of a clear oil. The oil was then carried forwarded as is. $^1$H-NMR (CDCl$_3$, 400 MHz): 5.72 (s, 2H), 4.95 (m, 1H, J=6.2 Hz), 1.33 (d, 6H, J=6.2 Hz). Note: Better yields are achieved when only 1.05 equivalents of dimethyl amino pyridine are used.

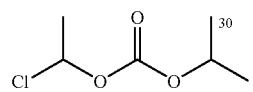

(+/−)-Carbonic acid 1-chloro-ethyl ester isopropyl ester was prepared analogous to carbonic acid chloromethyl ester isopropyl ester by substituting chloroethyl chloroformate (Fluka). $^1$H-NMR (CDCl$_3$, 400 MHz): 6.41 (q, 1H, J=5.8), 4.94 (m, 1H, J=6.2 Hz), 1.81 (d, 3H, J=5.8), 1.32 (m, 6H).

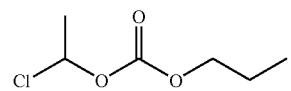

(+/−)-Carbonic acid 1-chloro-ethyl ester propyl ester was prepared analogous to carbonic acid chloromethyl ester isopropyl ester by substituting propanol (Aldrich). $^1$H-NMR (CDCl$_3$, 400 MHz): 6.41 (q, 1H, J=5.8), 4.17 (m, 2H), 1.81 (d, 3H, J=5.8), 1.71 (m, 2H), 0.96 (m, 3H).

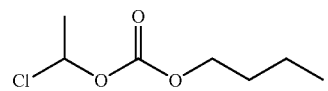

(+/−)-Carbonic acid butyl ester 1-chloro-ethyl ester was prepared analogous to carbonic acid chloromethyl ester isopropyl ester by substituting n-butanol (Aldrich). $^1$H-NMR (CDCl$_3$, 400 MHz): 6.41 (q, 1H, J=5.8), 4.20 (m, 2H), 1.81 (d, 3H, J=5.8), 1.67 (m, 2H), 1.41 (m, 2H), 0.93 (m, 3H).

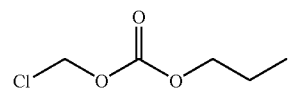

Carbonic acid chloromethyl ester propyl ester was prepared analogous to carbonic acid chloromethyl ester isopropyl ester by substituting propanol (Aldrich). $^1$H-NMR (CDCl$_3$, 400 MHz): 5.72 (s, 2H), 4.18 (t, 2H, J=6.6 Hz), 1.71 (m, 2H), 0.97 (t, 3H, J=7.5 Hz).

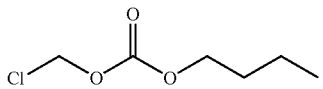

Carbonic acid butyl ester chloromethyl ester was prepared analogous to carbonic acid chloromethyl ester isopropyl ester by substituting n-butanol (Aldrich). $^1$H-NMR (CDCl$_3$, 400 MHz): 5.72 (s, 2H), 4.23 (t, 2H, J=6.6 Hz), 1.70 (m, 2H), 1.41 (m, 2H), 0.94 (t, 3H, J=7.5 Hz).

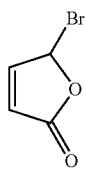

(+/−)-5-Bromo-5H-furan-2-one was prepared analogous to *Tett. Lett.* 22, 34, 1981, 3269–3272.

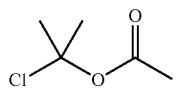

Acetic acid-1-chloro-1-methyl ethyl ester was Prepared as in Neuenschwander et al., *Helvetica Chimica* 1978; 61: 2047–2058.

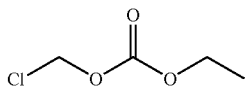

Carbonic acid chloromethyl ester ethyl ester was prepared analogous to carbonic acid chloromethyl ester isopropyl ester by substituting ethanol. $^1$H-NMR (CDCl$_3$, 400 MHz): 5.72 (s, 2H), 4.28 (q, 2H, J=7.1 Hz), 1.34 (t, 3H, J=7.1Hz).

EXAMPLE 8

Preparation of Comparison Prodrugs of 4-Thia-1-azabicyclo[3.2.0]heptane-2-carboxylicacid, 6-(hydroxymethyl)-3,3-dimethyl-7-oxo-, 4,4-dioxide (2S, 5R, 6R)

Prodrugs of 4-thia-1-azabicyclo[3.2.0]heptane-2-carboxylicacid, 6-(hydroxymethyl)-3,3-dimethyl-7-oxo-, 4,4-dioxide (2S, 5R, 6R) were prepared to demonstrate the unexpectedly improved bioavailability, and physical properties, of the prodrugs of the present invention. Of these Comparison Prodrugs, Comparison Prodrug 1 is described in Example 25 of U.S. Pat. No. 4,287,181. Comparison Prodrugs 2–15 are novel compounds but fall within the scope of the genus disclosed in U.S. Pat. No. 4,287,181.

Comparison Prodrug 1:

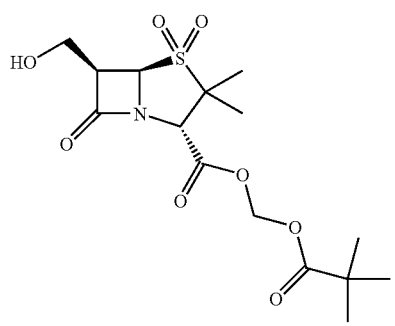

4-Thia-1-azabicyclo[3.2.0]heptane-2-carboxylic acid, 6-(hydroxymethyl)-3,3-dimethyl-7-oxo-, (2,2-dimethyl-1-oxopropoxy)methyl ester, 4,4-dioxide (2S, 5R, 6R)

To a stirred solution of 2.5 g (8.77 mmol.) 4-thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R) in 20 mL DMF was added (11.4 mmol.) chloromethyl pivalate (Aldrich) and stirred at room temperature overnight. The resulting mixture was then heated to 35° C. for 3 days. 40 mL water and 100 mL ethyl acetate were added and the layers were separated. The aqueous layer was extracted with ethyl acetate. The combined organic layers were washed with water, brine, dried over Na$_2$SO$_4$, filtered and concentrated in vacuo. Chromatography on silica gel eluting with 1 L of 20% ethyl acetate/80% hexanes followed by 1 L 1:1 ethyl acetate/hexanes yielded an oil. Hexanes (15 mL) were added to the oil and the sample was placed in the refrigerator for 4 days at which point a solid precipitated. It was then concentrated in vacuo yielding 110 mg of white amorphous solid. Melting point=70–73° C. $^1$H-NMR (CDCl$_3$, 400 MHz): 5.94 (d, 1H, J=5.4 Hz), 5.70 (d, 1H, J=5.4 Hz), 4.69 (d, 1H, J=4.1 Hz), 4.48 (s, 1H), 4.30 (m, 1H), 4.15 (m, 2H), 1.55 (s, 3H), 1.41 (s, 3H), 1.21 (s, 9H).

Alternately, this compound, which is also known as pivaloyloxymethyl 6-β-hydroxymethylpenicillinate sulfone, can be prepared as described in Example 25 of U.S. Pat. No. 4,287,181.

Comparison Prodrug 2:

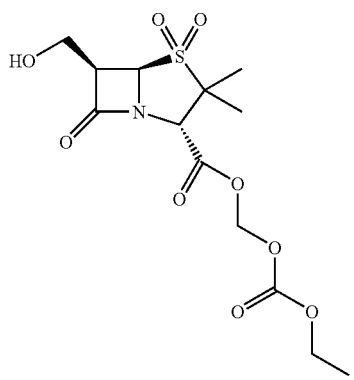

4-Thia-1-azabicyclo[3.2.0]heptane-2-carboxylic acid, 6-(hydroxymethyl)-3,3-dimethyl-7-oxo-, [(ethoxycarbonyl)oxy]methyl ester, 4,4-dioxide (2S, 5R, 6R)

This prodrug was prepared according to the method used to prepare Comparison Prodrug 1 with the exception that carbonic acid chloromethyl ester ethyl ester was substituted for chloromethyl pivalate. Melting point (amorphous solid) =103–105° C. ¹H-NMR (MeOD, 400 MHz): 5.91 (d, 1H, J=5.8 Hz), 5.76 (d, 1H, J=5.8 Hz), 4.96 (d, 1H, J=4.6 Hz), 4.55 (s, 1H), 4.15–4.25 (m, 4H), 3.95 (m, 1H), 1.53 (s, 3H), 1.41 (s, 3H), 1.29 (t, 3H, J=7.1).

Comparison Prodrug 3:

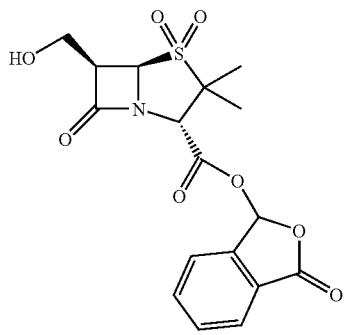

4-Thia-1-azabicyclo[3.2.0]heptane-2-carboxylic acid, 6-(hydroxymethyl)-3,3-dimethyl-7-oxo-, 1,3-dihydro-3-oxo-1-isobenzofuranyl ester, 4,4-dioxide (2S, 5R, 6R)

This prodrug was prepared according to the method used to prepare Comparison Prodrug 1 with the exception that 3-bromo phthalide (Aldrich) was substituted for chloromethyl pivalate.

Upon dilution of DMF with water the desired product precipitated as an amorphous solid and was filtered and dried in vacuo. MS (m/z):394 (M⁻) NMR represents a mixture of diastereomers. ¹H-NMR (d-DMSO, 400 MHz): 7.8–8.0 (m, 4H), 7.60 (s, 0.5H), 7.59 (s, 0.5H), 5.23 (m, 1H), 5.16 (OH), 4.71 (s, 0.5H), 4.67 (s, 0.5H), 4.20 (m, 1H), 4.02 (m, 1H), 3.74 (m, 1H), 1.47 (s, 1.5H), 1.37 (s, 1.5H), 1.36 (s, 1.5H), 1.31 (s, 1.5H).

Comparison Prodrug 4:

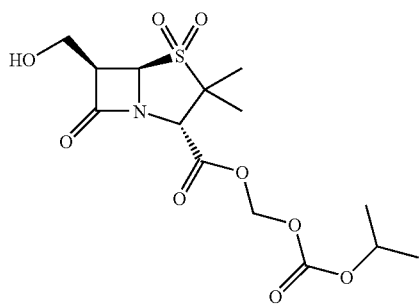

4-Thia-1-azabicyclo[3.2.0]heptane-2-carboxylic acid, 6-(hydroxymethyl)-3,3-dimethyl-7-oxo-, [[(1-methylethoxy)carbonyl]oxy]methyl ester, 4,4-dioxide (2S, 5R, 6R)

To a stirred solution of (18.4 mmol.) carbonic acid chloromethyl ester isopropyl ester in 200 mL acetone was added 13.8 g (92.1 mmol.) sodium iodide (Aldrich). The resulting mixture was stirred at room temperature overnight. To this solution was added 3.5 g (12.3 mmol.) 4-thia-1-azabicyclo[3,2,0]heptane-2-carboxylic acid, 6-(hydroxymethyl)-3,3-dimethyl-7-oxo-, 4,4-dioxide, monosodium salt, (2S, 5R, 6R) (U.S. Pat. No. 4,287,181) and the reaction mixture was stirred overnight at room temperature. The reaction mixture was then concentrated in vacuo. 200 mL water and 200 mL ethyl acetate were added and the organic layer was separated and washed with brine, dried over Na₂SO₄, filtered and concentrated in vacuo. Chromatography on silica gel eluting with 1:1 ethyl acetate/hexanes. The final product was a reddish oil. MS (m/z): 378 (M⁻). ¹H-NMR (d-DMSO, 400 MHz): 5.86 (d, 1H, J=5.8 Hz), 5.74 (d, 1H, J=5.8 Hz), 5.20 (d, 1H, J=5 Hz), 5.17 (m, OH), 4.82 (m, 1H), 4.60 (s, 1H), 4.20 (m, 1H), 4.03 (m, 1H), 3.74 (m, 1H), 1.42 (s, 3H), 1.30 (s, 3H), 1.22 (d, 6H, J=6.2 Hz).

Comparison Prodrug 5:

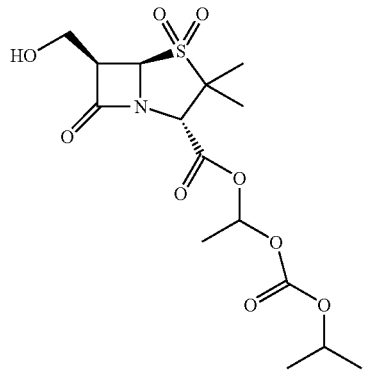

4-Thia-1-azabicyclo[3.2.0]heptane-2-carboxylic acid, 6-(hydroxymethyl)-3,3-dimethyl-7-oxo-, 1-[[(1-methylethoxy)carbonyl]oxy]ethyl ester, 4,4-dioxide (2S, 5R, 6R)

This prodrug was prepared according to the method used to prepare Comparison Prodrug 4 with the exception that carbonic acid 1-chloro-ethyl ester isopropyl ester was substituted for carbonic acid chloromethyl ester isopropyl ester. MS (m/z): 392 (M⁻). NMR is of a reddish oil that is a mixture of 2 diastereomers ¹H-NMR (d-DMSO, 400 MHz): 6.71 (q, 0.5H, J=5.4 Hz), 6.67 (q, 0.5H, J=5.4 Hz), 5.20 (d, 1H, J=5 Hz), 4.79 (m, 1H), 4.51 (s, 0.5H), 4.49 (s, 0.5H), 4.20 (m, 1H), 4.03 (m, 1H), 3.74 (m, 1H), 1.48 (m, 3H), 1.43 (s, 1.5H), 1.39 (s, 1.5H), 1.33 (m, 3H), 1.22 (m, 6H)

Comparison Prodrug 6:

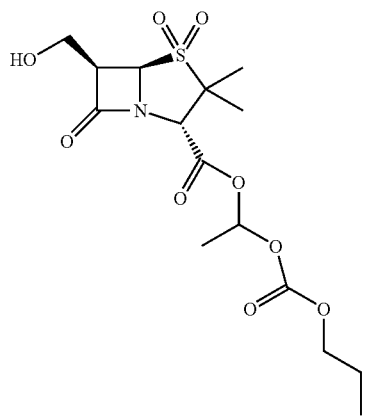

4-Thia-1-azabicyclo[3.2.0]heptane-2-carboxylic acid, 6-(hydroxymethyl)-3,3-dimethyl-7-oxo-, 1-[(propoxycarbonyl)oxy]ethyl ester, 4,4-dioxide (2S, 5R, 6R)

This prodrug was prepared according to the method used to prepare Comparison Prodrug 4 with the exception that carbonic acid 1-chloro-ethyl ester propyl ester was substituted for carbonic acid chloromethyl ester isopropyl ester. MS (m/z): 392 (M−). NMR is of a yellow-reddish oil that is a mixture of 2 diastereomers $^1$H-NMR (d-DMSO, 400 MHz): 6.72 (q, 0.5H, J=5.4 Hz), 6.68 (q, 0.5H, J=5.4 Hz), 5.20 (m, 1H), 4.51 (s, 0.5H), 4.49 (s, 0.5H), 4.20 (m, 1H), 4.03 (m, 3H), 3.74 (m, 1H), 1.59 (m, 2H), 1.48 (m, 3H), 1.39 (s, 1.5H), 1.34 (s, 1.5H), 1.22 (m, 3H), 0.86 (m, 3H).

Comparison Prodrug 7:

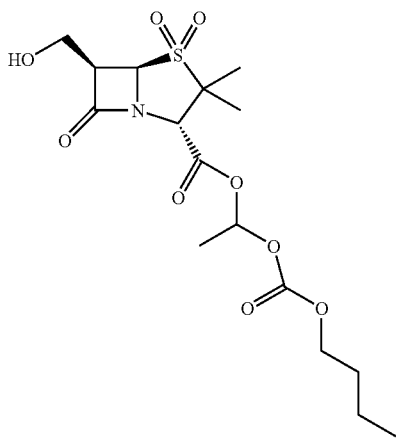

4-Thia-1-azabicyclo[3.2.0]heptane-2-carboxylic acid, 6-(hydroxymethyl)-3,3-dimethyl-7-oxo-, 1-[(butoxycarbonyl)oxy]ethyl ester, 4,4-dioxide (2S, 5R, 6R)

This prodrug was prepared according to the method used to prepare Comparison Prodrug 4 with the exception that carbonic acid butyl ester 1-chloro-ethyl ester was substituted for carbonic acid chloromethyl ester isopropyl ester. MS (m/z): 406 (M−). NMR is of a yellow-reddish oil that is a mixture of 2 diastereomers $^1$H-NMR (d-DMSO, 400 MHz): 6.72 (q, 0.5H, J=5.4 Hz), 6.68 (q, 0.5H, J=5.4 Hz), 5.20 (m, 1H), 4.51 (s, 0.5H), 4.49 (s, 0.5H), 4.20 (m, 1H), 4.03 (m, 3H), 3.74 (m, 1H), 1.59 (m, 2H), 1.15–1.55 (m, 11H), 0.86 (m, 3H).

Comparison Prodrug 8:

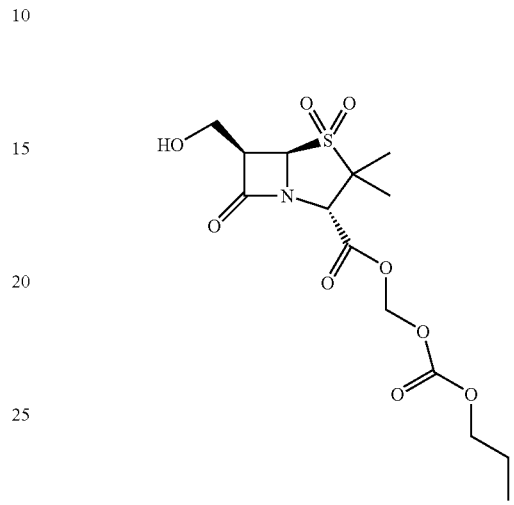

4-Thia-1-azabicyclo[3.2.0]heptane-2-carboxylic acid, 6-(hydroxymethyl)-3,3-dimethyl-7-oxo-, [(propoxycarbonyl)oxy]methyl ester, 4,4-dioxide (2S, 5R, 6R)

This prodrug was prepared according to the method used to prep isopropyl ester. The final product was an amorphous white solid. MS (m/z): 378 (M−). $^1$H-NMR (d-DMSO, 400 MHz): 5.86 (d, 1H, J=6.2 Hz), 5.74 (d, 1H, J=6.2 Hz), 5.20 (d, 1H, J=5 Hz), 5.17 (m, OH), 4.60 (s, 1H), 4.20 (m, 1H), 4.10 (m, 2H), 4.03 (m, 1H), 3.74 (m, 1H), 1.60 (m, 2H), 1.42 (s, 3H), 1.30 (s, 3H), 0.86 (t, 3H, J=7.5 Hz).

Comparison Prodrug 9:

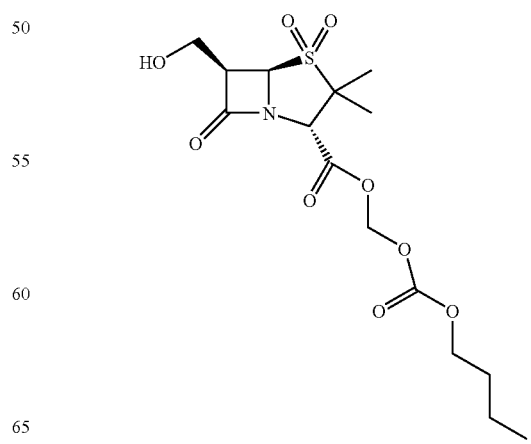

4-Thia-1-azabicyclo[3.2.0]heptane-2-carboxylic acid, 6-(hydroxymethyl)-3,3-dimethyl-7-oxo-, [(butoxycarbonyl)oxy]methyl ester, 4,4-dioxide (2S, 5R, 6R)

This prodrug was prepared according to the method used to prepare Comparison Prodrug 4 with the exception that carbonic acid butyl ester chloromethyl ester was substituted for carbonic acid chloromethyl ester isopropyl ester. The final product was an amorphous white solid. MS (m/z): 392 (M$^-$). $^1$H-NMR (d-DMSO, 400 MHz): 5.86 (d, 1H, J=6.2 Hz), 5.74 (d, 1H, J=6.2 Hz), 5.20 (d, 1H, J=5 Hz), 5.17 (m, OH), 4.60 (s, 1H), 4.20 (m, 1H), 4.15 (m, 2H), 4.03 (m, 1H), 3.74 (m, 1H), 1.60 (m, 2H), 1.42 (s, 3H), 1.30 (m, 2H), 1.30 (s, 3H), 0.86 (t, 3H, J=7.5 Hz).

Comparison Prodrug 10:

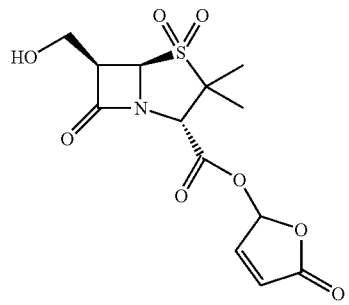

4-Thia-1-azabicyclo[3.2.0]heptane-2-carboxylic acid, 6-(hydroxymethyl)-3,3-dimethyl-7-oxo-, 2,5-dihydro-5-oxo-2-furanyl ester, 4,4-dioxide (2S, 5R, 6R)

This prodrug was prepared according to the method used to prepare Comparison Prodrug 4 with the exception that 5-bromo-5H-furan-2-one was substituted for chloromethyl pivalate. MS (m/z): 344 (M$^-$). NMR is a mixture of 2 diastereomers. The product was an amorphous solid. $^1$H-NMR (d-DMSO, 400 MHz): 7.81 (m, 0.5H), 7.73 (m, 0.5H), 7.14 (m, 0.5H), 7.10 (m, 0.5H), 6.61 (m, 1H), 5.21 (m, 1H), 5.17 (m, OH), 4.67 (s, 0.5H), 4.63 (s, 0.5H), 4.20 (m, 1H), 4.03 (m, 1H), 3.74 (m, 1H), 1.42 (s, 1.5H), 1.40 (s, 3H), 1.32 (s, 1.5H).

Comparison Prodrug 11:

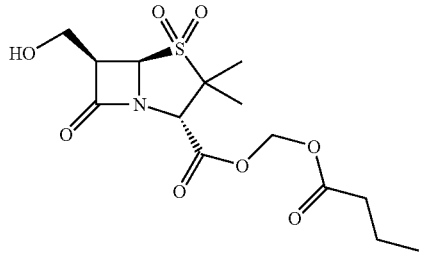

4-Thia-1-azabicyclo[3.2.0]heptane-2-carboxylic acid, 6-(hydroxymethyl)-3,3-dimethyl-7-oxo-, (1-oxobutoxy)methyl ester, 4,4-dioxide (2S, 5R, 6R)

This prodrug was prepared according to the method used to prepare Comparison Prodrug 4 with the exception that chloromethyl butyrate (Acros organics) was substituted for chloromethyl pivalate. The product was a clear oil. MS (m/z): 362 (M$^-$). $^1$H-NMR (d-DMSO, 400 MHz): 5.86 (d, 1H, J=5.8 Hz), 5.74 (d, 1H, J=5.8 Hz), 5.20 (d, 1H, J=5 Hz), 5.17 (m, OH), 4.55 (s, 1H), 4.20 (m, 1H), 4.01 (m, 1H), 3.74 (m, 1H), 2.35 (m, 2H), 1.52 (m, 2H), 1.40 (s, 3H), 1.30 (s, 3H), 0.86 (m, 3H).

Comparison Prodrug 12:

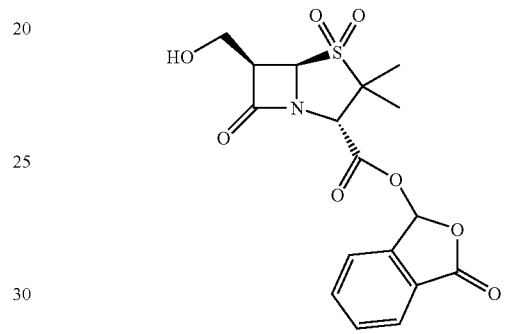

4-Thia-1-azabicyclo[3.2.0]heptane-2-carboxylic acid, 6-(hydroxymethyl)-3,3-dimethyl-7-oxo-, 1,3-dihydro-3-oxo-1-isobenzofuranyl ester, 4,4-dioxide (2S, 5R, 6R)

Prepared by chromatography on silica gel of 275 mg of Comparison Prodrug 3 using 5% isopropyl alcohol/95% methylene chloride yielded 200 mg of a mixture of diastereomers followed by 70 mg of a single, (more polar) diastereomer. The product was an amorphous solid. MS (m/z): 394 (M$^-$) NMR represents the more polar diastereomer. $^1$H-NMR (d-DMSO, 400 MHz): 7.95 (d, 1H, J=7.5 Hz), 7.90 (m, 1H), 7.81 (d, 1H, J=7.5 Hz), 7.77 (m, 1H), 7.60 (s, 1H), 5.23 (d, 1H, J=5 Hz), 5.16 (OH), 4.71 (s, 1H), 4.20 (m, 1H), 4.02 (m, 1H), 3.74 (m, 1H), 1.47 (s, 3H), 1.37 (s, 3H).

Comparison Prodrug 13:

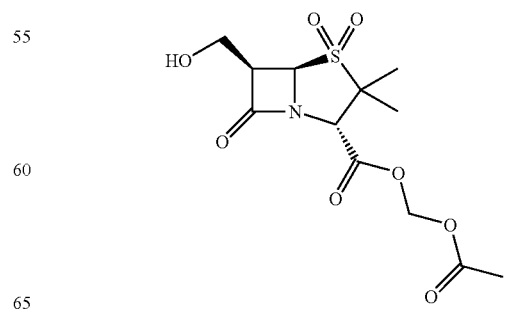

4-Thia-1-azabicyclo[3.2.0]heptane-2-carboxylic acid, 6-(hydroxymethyl)-3,3-dimethyl-7-oxo-, (acetyloxy)methyl ester, 4,4-dioxide (2S, 5R, 6R)

This prodrug was prepared according to the method used to prepare Comparison Prodrug 1 with the exception that bromomethyl acetate (Aldrich) was substituted for chloromethyl pivalate. The final product was a viscous oil. MS (m/z): 334 (M⁻). ¹H-NMR (d-DMSO, 400 MHz): 5.82 (d, 1H, J=6.2 Hz), 5.72 (d, 1H, J=6.2 Hz), 5.19 (d, 1H, J=5 Hz), 5.17 (m, OH), 4.55 (s, 1H), 4.20 (m, 1H), 4.01 (m, 1H), 3.74 (m, 1H), 2.08 (s, 3H), 1.40 (s, 3H), 1.30 (s, 3H).

Comparison Prodrug 14:

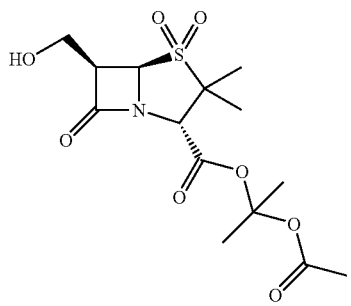

4-Thia-1-azabicyclo[3.2.0]heptane-2-carboxylic acid, 6-(hydroxymethyl)-3,3-dimethyl-7-oxo-, 1-(acetyloxy)-1-methylethyl ester, 4,4-dioxide (2S, 5R, 6R)

This prodrug was prepared according to the method used to prepare Comparison Prodrug 1 with the exception that acetic acid-1-chloro-1-methyl ethyl ester was substituted for chloromethyl pivalate. The final product was an amorphous solid. MS (m/z): 362 (M⁻). ¹H-NMR (CDCl₃, 400 MHz): 4.68 (d, 1H, J=5.0Hz), 4.40 (s, 1H), 4.31 (m, 1H), 4.15 (m, 2H), 2.06 (s, 3H), 1.92 (s, 3H), 1.82 (s, 3H), 1.58 (s, 3H), 1.47 (s, 3H).

EXAMPLE 9

Chemical (pH), Suspension and Plasma Stability

The stability of Prodrug 3 was evaluated with regards to (1) chemical stability while in solutions of various pH, (2) maintaining potency while in suspension, and (3) chemical stability in plasmas from various mammals to assess the ability of Prodrug 3 to resist hydrolysis prior to absorption and then to rapidly hydrolyze to form 6-β-HMPAS after absorption.

Chemical stability of Prodrug 3, in solution, as compared to the sodium salt of 6-β-HMPAS (hereinafter "Na HPMAS") and lithium clavulanate in solution, was assessed at pH 1, 2, 2.5, 4.0, 5.0, 6.5, and 7.4. Buffers were appropriately formulated to achieve the desired pH of each incubation. The incubation consisted of 990 µl of the appropriate pH buffer and was initiated with the addition of 10 µl of a 10 mM stock of compound in 100% methanol (final concentration=100 µM). Serial samples (20 µl) were taken at 0, 10, 20, 40, 60, 120, and 240 minutes by an auto injector and injected directly onto an HPLC in-line with a LC/MS single quadropole mass spectrometer system used for analyte detection. The temperature of the incubation was regulated with a 96-well heat block. Incubations were performed at 25° C. and 37° C. The LC/MS system was run in the negative ion mode. Selective ion monitoring of the appropriate [M–H]⁻ for each analyte was used for detection and quantitation of remaining compound at each timepoint. The peak response at each time point was expressed as a percentage of that obtained at time=0. A degradation rate constant ($k_d$) was obtained by regression of these percentages from time=0 minutes to time=240 minutes. An apparent first-order half-life could then be estimated as ln 2/$k_d$. These determinations were completed in duplicate and the average was reported.

As shown in the following table, Prodrug 3 demonstrated excellent acid stability and adequate stability near neutral pH for absorption. Also, Na-HMPAS demonstrated superior solution stability compared to clavulanate, particularly at low pH.

The stability of Prodrug 3 in suspension (un-buffered in 0.5% methylcellulose at 25° C.) was also evaluated to determine the effect of time in suspension upon potency. As shown below, Prodrug 3 maintained greater than 90% of its potency after storage at room temperature for 10 days. By contrast, only 40% of potency is retained with clavulanate in the Augmentin suspension if left at room temperature for the same time period (See Mehta, A. C., S. Hart-Davies, J. Payne and R. W. Lacey, 1994. Stability of amoxicillin and potassium clavulanate in a co-amoxicillin-clavulanate oral suspension. *J. Clin. Pharm. Ther.* 19:313–315.).

|  | pH | | | | | |
| --- | --- | --- | --- | --- | --- | --- |
| Solution Stability (100 µM) | 7.4 | 6.5 | 5.0 | 4.0 | 2.5 | 1.2 |
|  | Half-life (Hours) | | | | | |
| Prodrug 3 (25° C.) | 2.7 | >24 | >24 | >24 | >24 | >24 |
| Prodrug 3 (37° C.) | 0.6 | 4.5 | >24 | >24 | >24 | >24 |
| Na-HMPAS (25° C.) | >24 | >24 | >24 | >24 | >24 | >24 |
| Na-HMPAS (37° C.) | >24 | >24 | >24 | >24 | >24 | >24 |
| Clavulanate (25° C.) | >24 | >24 | >24 | >24 | 1.2 | 0.6 |
| Clavulanate (37° C.) | >24 | >24 | >24 | >24 | 0.9 | ND |
| Prodrug 3 Suspension Stability | Day 1 | Day 3 | Day 5 | Day 7 | Day 10 | |
|  | Potency (percent)* | | | | | |
| 1.51 mg/ml** (10 mg/kg rat dose preparation) | ND | 103 | 98 | 104 | 91*** | |

*Potency assessed as a percentage of the target concentration as assayed by LC/MS of solubilized standards. Values represent an average of duplicate determinations.
ND = not determined
**pH of initial suspensions ~6.8 and fell to 4.7 by day 10
***diastereomer mixture essentially unchanged ~95:5

Plasma stability of Prodrug 3, Na-HMPAS and lithium clavulanate were determined, in mouse, rat, dog, monkey and human plasma, using plasma that was prepared and subjected to one freeze/thaw cycle prior to use. The incubation consisted of 990 µl of plasma preincubated for 5 minutes at 37° C. in a 96-well heat block. The incubation was initiated with the addition of 10 µl of a 10 mM stock of compound in 100% methanol. Serial aliquots (100 µl) were removed and transferred to 200 µl of 75/25 acetonitrile/3% perchloric acid at 0, 1, 2, 5, 10, 20, 30, and 60 minutes. The samples were centrifuged, the supernatants transferred to injection vials, and 20 µl was injected onto the HPLC in-line with a LC/MS single quadropole mass spectrometer. The LC/MS system was run in the negative ion mode. Selective ion monitoring of the appropriate [M–H]⁻ for each analyte was used for detection and quantitation of remaining compound at each timepoint. The peak response at each time point was expressed as a percentage of that obtained at time=0. A degradation rate constant ($k_d$) was obtained by regression of these percentages from time=0 minutes to time=240 minutes. An apparent first-order half-life was then be estimated as ln $2/k_d$. These determinations were completed in duplicate and the average was reported as shown below.

| Plasma Stability (100 µM) | Half-life | | | | |
|---|---|---|---|---|---|
| | Mouse | Rat | Dog | Monkey | Human |
| Prodrug 3 37° C. | 2.8 min | <2.0 min | 2.8 min | 3.6 min | <2.0 min |
| Na-HMPAS 37° C. | 3.9 hr | 3.4 hr | >4 hr | >4 hr | >4 hr |
| Clavulanate 37° C. | >4 hr | 3.3 hr | 2.8 hr | 3.6 hr | 2.6 hr |

Prodrug 3 demonstrated excellent acid stability and adequate stability near neutral pH for absorption. Hydrolysis rates of Prodrug 3 in the plasma of all species tested, demonstrate efficient enzymatic hydrolysis to yield 6-β-HMPAS upon absorption. Na-HMPAS demonstrated superior solution stability compared to clavulanate, particularly at low pH. Although both compounds are labile in plasma, Na-HMPAS shows improved human plasma stability.

EXAMPLE 10

Inhibitory Activity of Prodrug 3 at Intestinal pH Values

It is thought that clavulanate produces diarrhea in the human GI tract since it combines with residual amoxicillin to selectively kill essential components of the normal flora. Clavulanate is not a prodrug, and thus the 40% that remains unabsorbed from the intestine is the same active molecule as the 60% that is absorbed into circulation. While the pH of the stomach and proximal small intestine is acidic, in a study by Berry, V. et al., *Efficacy of a pharmacokinetically enhanced formulation of amoxicillin/clavulanate against experimental respiratory tract infection in rats caused by Streptococcus pneumoniae*, Abstract B988, 41$^{st}$ Interscience Conference on Antimicrobial Agents and Chemotherapy, Dec. 16–19$^{th}$, 2001 Chicago, Ill., found that the median pH of 24 h stool samples collected from subjects with diarrhea was 6.4 (range 5.4–7.8).

As shown in Example 7, Prodrug 3 is very stable and does not readily convert to 6-β-HMPAS at pH<6.5. In order to compare the beta-lactamase inhibitory activity of Prodrug 3 and Na-HMPAS under pH conditions found in the human large intestine, we determined the IC$_{50}$ of both compounds against a TEM-1 beta-lactamase at pH 6.0 and 7.0. The data indicate that at pH 6.0, where there should be no conversion of the prodrug to the active form of the inhibitor, Prodrug 3 is inactive against TEM-1 beta-lactamase (IC$_{50}$>100 µM). In contrast, at pH 7.0 where conversion of the prodrug to active inhibitor occurs with a half-life of 33 minutes, the resulting 6-β-HMPAS generated results in a much greater level of inhibition of this beta-lactamase than was observed at pH 6.0.

| | IC$_{50}$ (µM) | |
|---|---|---|
| | Prodrug 3 | 6-β-HMPAS |
| *E. coli* TEM-1 pH 6.0 | >100 | 0.37 |
| *E. coli* TEM-1 pH 7.0 | 2.2 | 0.12 |

EXAMPLE 11

Absorption (Oral In Vivo Bioavailability)

As Prodrug 3 has a solution half-life of 30 minutes at neutral pH and, in the presence of esterases, the prodrug is hydrolyzed within a few minutes, an in vitro assessment using the human Caco-2 cell line was determined to be inappropriate to measure prodrug absorption. Instead, an in vivo model for absorption was found to be more relevant for assessing absorption of the prodrugs of the present invention. Further, the correlation of fraction absorbed in the rat to that of human has been studied in several marketed agents and the correlation has been shown to be quite good (corr=0.971) (See Chiou, W. L. and A. Barve, 1998. Linear correlation of the fraction of oral dose absorbed of 64 drugs between humans and rats. *Pharm. Res.* 15:1792–1795.). Based upon this correlation, the rat was used to predict human absorption. It should be further appreciated that 6-β-HMPAS demonstrated minimal hepatic extraction as suggested by rat and human hepatocytes. Thus, oral bioavailability assessments in rats should correlate well with the fraction absorbed in humans.

Estimates of oral bioavailability were conducted on Na-HMPAS, Prodrugs 1, 2, 3 and 4, as well as the fourteen comparison prodrugs of Example 8, each using sets of three Sprague-Dawley rats (200–225 gm) equipped with surgically implanted jugular vein catheters. The selection of dose vehicles, for the oral studies, depended upon the physical state of the compound being tested. All compounds that were orally administered, with the exception of Prodrug 1, were in the form of an oil or an amorphous solid. As such, these compounds were administered in a solution (PO) dosage form using a 70/20/10 water/Chremophore/ethanol vehicle.

The oral prodrug doses were prepared to deliver a 10 mg/kg equivalent dose of 6-µ-HMPAS at a dose volume of 10 ml/kg. Na-HMPAS was administered intraveneously at a dose of 10 mg/kg to establish bioavailability estimates (6-µ-HMPAS equivalent).

Blood samples were taken at 0, 15, 30 min., 1, 2, 3, and 5 hr. after dosing. The samples were then processed for plasma and stored at –20° C. prior to analysis. Samples were assayed for 6-β-HMPAS, as described below, and then the mean concentration versus time profiles for oral and intravenous administration were determined. The area under the plasma concentration versus time curve (AUC$_{0\text{-}tlast}$) was calculated from time 0 to the last quantifiable timepoint using linear trapezoidal approximation. The terminal elimination rate constant ($K_{el}$) was estimated by regression of the plasma concentration data from the apparent beginning of the elimination phase to the last sample point. An elimination half-life was estimated as ln 2/Kel. The area from tlast to infinity (AUC$_{tlast\text{-}\infty}$) was estimated at Cest$_{tlast}$/K$_{el}$ where Cest$_{tlast}$ represents the estimated concentration at the last time point in which drug was quantified based on the regressional analysis. The total area under the curve (AUC$_{0-\infty}$) was estimated as the sum of AUC$_{0-tlast}$ and AUC$_{tlast-\infty}$. Bioavailability (F) was expressed as AUC$_{(0-\infty)po}$×Dose$_{iv}$/AUC$_{(0-\infty)iv}$×Dose$_{po}$.

The mean bioavailabilities found were as shown below.

| Compound | Mean Bioavailability | Standard Deviation |
| --- | --- | --- |
| Na-HMPAS | 6.0 | 1.6 |
| Prodrug 1 | 113.1 | 10.7 |
| Prodrug 2 | 102.0 | 11.1 |
| Prodrug 3 | 92.4 | 6.0 |
| Prodrug 4 | 111.1 | 8.8 |
| Comparison Prodrug 1 | 55.4 | 4.7 |
| Comparison Prodrug 2 | 6.2 | 1.0 |
| Comparison Prodrug 3 | 27.2 | 2.6 |
| Comparison Prodrug 4 | 6.8 | 0.9 |
| Comparison Prodrug 5 | 46.5 | 1.4 |
| Comparison Prodrug 6 | 60.9 | 6.1 |
| Comparison Prodrug 7 | 40.3 | 10.8 |
| Comparison Prodrug 8 | 7.9 | 1.5 |
| Comparison Prodrug 9 | 12.3 | 2.0 |
| Comparison Prodrug 10 | 10.9 | 1.7 |
| Comparison Prodrug 11 | 33.1 | 5.4 |
| Comparison Prodrug 12 | 20.4 | 1.0 |
| Comparison Prodrug 13 | 37.6 | 3.7 |
| Comparison Prodrug 14 | 15.4 | 3.9 |

As shown above, the prodrugs of the present invention have significantly better bioavailabilities than does 6-β-HMPAS, the previously known Comparison Prodrug 1, or the prior generically disclosed prodrugs (Comparison Prodrugs 2–14).

Assay Description:

In this assay, the analytes of interest were back extracted into the aqueous phase following acetonitrile precipitation and treatment with chloroform. This provided approximately a 2 fold concentration factor without having an evaporation and reconstitution step.

Detection was afforded through the use of LC/MS/MS in negative ion operation. Single quadrapole operation was inadequate for selective detection of the analyte.

The pH of the loading solvent (95:5 20 mM ammonium formate/acetonitrile; solvent A) was ,72~5.0.

The analytical column was an Pheneomenex AQUA C18 4.6×50 mm.

All sample preparation was completed in 96-well 1.2 mL MARSH-tubes. The samples were prepared as follows. The Plasma sample (200 μl) was added to 400 μl of 95:5 acetonitrile: 20 mM ammonium formate containing 5 μg/ml sulbactam as an internal standard. The samples were centrifuged at 3000 rpm for 10 min in a table top centrifuge. The supernatant (400 μl) was then transferred to clean 1.2 ml MARSH® tubes. Chloroform (600 μl) was added to the samples, which were then mixed, and subsequently centrifuged at 3000 rpm for 10 minutes. The transferred aqueous phase was then removed from top (~100 μl) and then analyzed.

Mass Spectrometry Conditions:
Mass Spectrometer: API-3000 operated in negative ion mode using Turbo spray (electrospray)
Ionization voltage: −3000V
Orifice voltage: −25 eV
Collision energy: 30 eV
Nebulization and Heat gas adjusted as needed
Reaction Monitoring:
6-β-HMPAS: 262=>218
Sulbactam (IS): 232=>140
Amoxicillin: 364=>223
Clavulanic acid: 198=>136
Run time: 3 min.
RT: ~2 min for all analytes
Injection Volume: 20 μl
HPLC Conditions:
Solvent A: 95:5 20 mM ammonium formate: acetonitrile
Solvent B: 95:5 acetonitrile: 20 mM ammonium formate
Analytical Flow: 1 ml/min
Flow to Mass Spectrometer: ~100 μl/min
Ballistic Gradient Schedule:
0–0.5 min 100% A
0.5–1 min 100% A to 100% B
1–1.5 min 100% B
1.5–2.0 min 100% B to 100% A
LLOQ=0.1 μg/ml for 6-β-HMPAS and amoxicillin, 0.5 μg/ml clavulanic acid
ULOQ=50 μg/ml (All)
Regression=linear 1/x weighting
Column life~300–400 injections Portal Vein Studies in Rats: Systemic exposure of Prodrug 3 was also assessed in portal vein cannulated rats following oral administration of the prodrug at a dose of 100 mg/kg. Whole blood aliquots were stabilized in ice cold acid immediately upon sampling at 5, 15 and 30 minutes post dose. No levels of Prodrug 3 were detected in any of the samples (assay LLOQ of 100 ng/ml). These results suggest that upon absorption, Prodrug 3 undergoes rapid hydrolysis to yield 6-β-HMPAS prior to exposure to the liver and circulation throughout the body.

EXAMPLE 12

In Vitro Screens

Biochemical activity against β-lactamases from community respiratory pathogens: Only three beta-lactamase inhibitor molecules exist in the marketplace: sulbactam, clavulanate and tazobactam. All three inhibit type A penicillinases found in a broad range of bacteria. Of these, only clavulanate is directed toward oral therapy of community respiratory infections. Na-HMPAS was tested against a collection of cell-free penicillinases commonly found in *H. influenzae* and *M. catarrhalis* that are resistant to ampicillin. The data in the following table indicates that Na-HMPAS is equivalent to lithium clavulanate against the ROB-1 and TEM-1 enzymes from *H. influenzae*. All three beta-lactamase inhibitors were very potent against the BRO-1 and BRO-2 penicillinases found in *M. catarrhalis*, with sulbactam being the most active (Table 1). A broader analysis of β-lactamases from 30 recent clinical isolates of *M. catarrha-* lis showed that Na-HMPAS was effective at inhibiting the BRO-1 and BRO-2 enzymes from all of these strains, with an average $IC_{50}$ of 0.19 μM.

IC$_{50}$s of β-lactamase inhibitors against β-lactamases in cell extracts

| Strains | β-lactamase Type | $IC_{50}$ (μM)* | | |
|---|---|---|---|---|
| | | Sulbactam | 6-β-HMPAS | Clavulanate |
| H. influenzae ATCC43334 | ROB-1 | 3.40 | 0.01 | 0.04 |
| H. influenzae 54A1173 | TEM-1 | 4.78 | 0.03 | 0.02 |
| M. catarrhalis 87A1178 ATCC43617 | BRO-2 | 0.03 | 0.32 | 0.11 |
| M. catarrhalis 87A1115 | BRO-1 | 0.011 | 0.143 | 0.14 |

*All inhibitory values are determined against the chromogenic cephalosporin in a colorimetric assay.

Biochemical activity against β-lactamases from other pathogens, including those associated with skin infections: Na-HMPAS was comparable to clavulanate in terms of its inhibitory potency against a wide variety of TEM extended spectrum beta-lactamases (ESBLs) while Na-HMPAS and clavulanate were usually comparable in potency against ESBLs.

Inhibition of selected extended spectrum β-lactamases (ESBLs) ($IC_{50}$, μM) Inhibitor

| Strains | β-lactamase Type | $IC_{50}$ (μM)* | | |
|---|---|---|---|---|
| | | Sulbactam | 6-β-HMPAS | Clavulanate |
| E. coli ATCC35218 | TEM-1 | 6.85 | 0.14 | 0.05 |
| E. coli 51A1101 | TEM-1 | 4.76 | 0.07 | 0.02 |
| K. pneumoniae CF104 | TEM-3 | 0.55 | <0.003 | <0.003 |
| K. pneumoniae CF504 | TEM-5 | 4.68 | 0.08 | <0.003 |
| K. pneumoniae B L-1 | TEM-10 | 23.19 | 0.39 | >100 |
| K. pneumoniae MCV37 | TEM-12 | 5.86 | 0.27 | <0.003 |
| K. pneumoniae CF1304 | TEM-16 | 5.80 | 0.09 | 0.06 |
| K. pneumoniae E264 | TEM-17 | 10.36 | 0.66 | 0.004 |
| K. pneumoniae CF1104 | TEM-24 | 10.48 | 7.13 | 0.01 |
| E. coli CF1609 | TEM-25 | 2.58 | 0.04 | 0.02 |
| K. pneumoniae 5657 | TEM-26 | 0.56 | 0.08 | 0.02 |
| Serratia S6 | Sme-I | 15.65 | 0.68 | 19.55 |

*All inhibitory values are determined against the chromogenic cephalosporin in a colorimetric assay.

In general, it can be concluded that Na-HMPAS is comparable to lithium clavulanate.

Susceptability assay for β-lactamase producing species H. influenzae and M. catarrhalis: The in vitro activity of various ratios of 6-β-HMPAS and amoxicillin was assessed using clinical isolates of H. influenzae and M. catarrhalis that produce β-lactamase. The NCCLS (National Committee for Clinical Laboratory Standards) approved susceptibility method for Augmentin uses a fixed 2:1 ratio of amoxicillin/clavulanate. The results indicated that for 46 beta-lactamase (+) strains of H. influenzae, the amoxicillin $MIC_{50}$ and $MIC_{90}$ values (i.e., the minimal inhibitory concentrations required to prevent the growth of either 50% or 90% of the isolates tested) for both amoxicillin/clavulanate and amoxicillin/6-β-HMPAS were 1 and 2 μg/ml, respectively, while the values for 2:1 amoxicillin/sulbactam were 4 and 8 μg/ml. Note that the numbers refer to the amoxicillin concentration in the mixture.

For 48 isolates of M. catarrhalis, the $MIC_{50}$ and $MIC_{90}$ values for amoxicillin/clavulanate were ≦0.125 and 0.25 μg/ml, and 0.5 and 1.0 μg/ml for amoxicillin/6-β-HMPAS, respectively. Values for amoxicillin/sulbactam (2:1) were 0.25 and 1.0 μg/ml. Thus, MICs obtained with whole cells do not always correlate well with inhibitor potencies against cell-free beta-lactamases, as sulbactam was consistently more potent against the BRO-1/2 enzymes found in M. catarrhalis.

Susceptability assay for Non-β-lactamase producing species Streptococcus pneumoniae: The in vitro activity of the combination was compared with that observed with amoxicillin alone against clinical isolates of S. pneumoniae that were classified as penicillin-susceptible, -intermediate and -resistant. Some of these strains showed high-level resistance to penicillin and amoxicillin with MICs in the 4–8 μg/ml range. As expected for a pathogen with PBP-based resistance, results for isolates of S. pneumoniae confirmed that the presence of inhibitors had no influence on amoxicillin MICs.

The amoxicillin $MIC_{50}$s and $MIC_{90}$s for 21 penicillin-resistant strains (penicillin MICs from 1–8 μg/ml) were 2 and 4 μg/ml for amoxicillin alone and for all beta-lactamase inhibitor combinations tested at amoxicillin/inhibitor ratios of 2:1, 7:1 and 14:1. Finally, all combinations were tested against a group of 21 penicillin-intermediate S. pneumoniae and 12 penicillin-susceptible isolates. Again, all of the MICs in both groups reflected the amoxicillin component of the combination. Amoxicillin MICs for the intermediate group ranged from 0.03 to 1 μg/ml and the MICs for the susceptible group were ≦0.0156 to 0.06 μg/ml.

Assay Methodology: The assay was performed according to the method described in NCCLS Document M7-A4, December 1997 and M100-S12, 2002, Methods for Dilution Antimicrobial Susceptibility Tests for Bacteria that Grow Aerobically-Approved Standard.

PREPARATION OF FROZEN STOCKS: H. influenzae are grown on chocolate agar plates. Colonies are suspended into Haemophilus test medium (HTM, Remel Diagnostics) which has been pH adjusted to 7.4 with 1N NaOH and filter sterilized. This is mixed with 50% glycerol to a final concentration of 20% glycerol. Growth of Streptococcus pneumoniae and Moraxella catarrhalis is scraped off sheep blood agar plates and placed into Mueller Hinton broth plus 5% lysed sheep blood. For freezing, 50% glycerol is added to a final concentration of 20%. All are frozen at −70° C.

PREPARATION OF DRUG PLATES: 96-well microtiter plates are used for the drug dilutions. All drugs are weighed out in sufficient quantity to make a 4× working stock solution. Drug is solubilized in DMSO or other appropriate solvent, dissolved to volume in testing medium, and 100 μl is serially diluted twofold through a series of 10 drug wells each containing an initial volume of 100 μl medium [columns 1 through 10] and 1 drug well with no inoculum [column 11]. Column 12 is a bacterial inoculum control well containing no drug. Final volume in each well is 100 μl.

Drug plates for *H. influenzae* are serially diluted in HTM which has been pH adjusted to 7.4 with 1 N NaOH and filter sterilized. The other two species are diluted in Mueller Hinton broth plus 5% lysed horse blood. Control compounds are run with each assay. Drug plates are frozen at ~−70° C. and thawed on the day of use.

GROWTH OF INOCULUM: *H. influenzae* are grown overnight on Mueller Hinton agar plates with 1% hemoglobin and with 1% GCHI [chocolate agar plates] in a 5% $CO_2$ incubator overnight at 37° C. *S. pneumoniae* and *M. catarrhalis* are grown on Mueller Hinton agar containing 5% sheep blood under the same conditions.

PREPARATION OF INOCULUM: Overnight growth from an agar plate was taken and resuspended in the appropriate test medium. All suspensions were adjusted to a standard OD by spectrophotometry on the day of the assay using Haemophilus test medium (HTM) broth for *H. influenzae* or cation supplemented Mueller Hinton broth plus 5% lysed horse blood (for *S. pneumoniae* and *M. catarrhalis*) to a turbidity corresponding to a 0.5 McFarland standard suspension (about 1 to $2\times10^8$ CFU/ml). This suspension had an $OD_{625}$ of 0.14. To obtain a final inoculum of $2–7\times10^5$ cfu/ml in the well (final volume of 200 μl), the following dilutions were made from the McFarland stock:

All *H. influenzae* strains were diluted 1/100 in HTM.

All *S. pneumoniae* and *M. catarrhalis* were diluted 1:100 in cation supplemented Mueller Hinton broth containing 5% lysed horse blood.

INOCULATION OF PLATES: 100 μl of the diluted inoculum is added to each 100 μl of diluted drug in the sterile test plate. Total volume for the test is 200 μl per well. Strains that have been diluted appropriately (see above) into microtiter wells will have a final inoculum of 2 to $7\times10^5$ CFU/ml. These cell inocula are confirmed on random plates by performing viability counts of the wells at zero time. This is easily done by removing 10 μl from the well and diluting it in 10 ml of sterile, physiological saline (1:1000 dilution). After vortexing, 100 μl of the diluted suspension is spread on a blood agar plate or a chocolate agar plate in the case of *H. influenzae*. Following incubation, the presence of 50 colonies indicates an inoculum density of $5\times10^5$ CFU/ml. Cultures used for inocula into the microtiter trays are streaked for single colonies and observed for typical colony morphology.

INCUBATION OF MICROTITER PLATES: After placing plastic lids on the plates, microtiter plates are incubated in plastic boxes in a controlled humidity incubator to prevent evaporation from the wells. Plates are stacked no more than 4 high. All microtiter plates are incubated aerobically at 35° C. for 24 hours.

All plates are incubated and read after 24 hours and results are recorded only if the control drugs for the NCCLS type strain *H. influenzae* ATCC 49766 and *S. pneumoniae* ATCC 49619 is within the published range (NCCLS, M100-S12, 2002).

EXAMPLE 13

In Vivo Efficacy

The in vivo β-lactamase inhibitory activity of 6-β-HMPAS was determined for the β-lactamase (+) pathogens that were evaluated in our pre-clinical infection models. The data for these selected isolates indicated that 6-β-HMPAS is generally equivalent to clavulanate for β-lactamases from the respiratory pathogens *H. influenzae* and *M. catarrhalis*.

Gerbil otitis media model: In this model, Mongolian gerbils were challenged with *S. pneumoniae* or *H. influenzae*. Female Mongolian gerbils (50–60 g) were challenged with log 5–6 CFU of *H. influenzae* or *S. pneumoniae* delivered in a 50 μL volume into the left tympanic bulla. Eighteen hours post-challenge, a dose-response therapeutic regimen was initiated (t.i.d. for 2 days) with the combination of Amoxicillin and Prodrug 3 (7:1) delivering the dosage in a 500 uL volume of 0.5% methylcellulose vehicle. ED50s were calculated from bacterial clearance data on day 4 post-challenge.

The amoxicillin/Prodrug 3 and Augmentin combinations were equally effective in clearing this pathogen with $ED_{50s}$ of 6–10 mg/kg, and outcomes for the 7:1 and 14:1 combinations were equivalent. Amoxicillin as a single agent failed against this pathogen.

Murine systemic infection model: In this model, Female CF-1 or DBA/2 mice (18–20 g) were challenged intraperitoneally with log 2–6 CFU of *S. pneumoniae*, *S. aureus* or *M. catarrhalis* suspended in broth, 10% mucin or 3% Brewers yeast, respectively, and delivered in a 500 μL volume. One hour post-challenge, a dose-response therapeutic regimen was initiated (b.i.d. for 1 day) with the combination of Amoxicillin/Prodrug 3 (7:1) delivering the dosage in a 200 μL volume of 0.5% methylcellulose vehicle. ED50s were calculated from the survival data on day 4 post-challenge.

The combination of amoxicillin/Prodrug 3 was effective in protecting mice from death from all of these β-lactamase (+) strains. In general, the activity of the amoxicillin/Prodrug 3 combination was comparable to that of Augmentin (i.e. equivalent versus *H. influenzae* and slightly less against *M. catarrhalis*). The 7:1 combinations were generally more effective than the 14:1 combinations. Data for the skin and skin structure pathogens *S. aureus*, *K. pneumoniae* and *E. coli* are also included in the following tables.

Murine pneumonia model: In this model, Female CF-1 (18–20 g) were challenged intranasally with log 5-6 CFU of *S. pneumoniae* delivered in a 40 μL volume and eighteen hours post-challenge, a dose-response therapeutic regimen was initiated (b.i.d. for 2 days) with the combination of Amoxicillin/Prodrug 3 (7:1) delivering the dosage in a 200 μL volume of 0.5% methylcellulose vehicle. ED50s were calculated from the survival data on day 10 post-challenge.

Amoxicillin, amoxicillin/Prodrug 3 and Augmentin were equally effective against a penicillin-tolerant ($PD_{50}s$ of 22–25 mg/kg) and penicillin-susceptible pneumococcal strain ($PD_{50}s$ of 2.7–3.3 mg/kg). Since penicillin-tolerant strains of pneumococci do not harbor a β-lactamase, the activity of amoxicillin is not improved (nor is it antagonized) by the presence of 6-β-HMPAS or clavulanate. The higher $PD_{50}s$ noted with the penicillin-tolerant strain relative to the penicillin-susceptible strain is consistent with the higher MIC.

In summary, the in vivo oral activity for the combination of amoxicillin/Prodrug 3 (7:1 and 14:1) was compared in a head-to-head fashion with Augmentin in a gerbil otitis media model and mouse models of peritonitis and pneumonia. The amoxicillin/Prodrug 3 combination demonstrated comparable in vivo activity to that of Augmentin vs. respiratory tract pathogens (*H. influenzae*, *M. catarrhalis* and *S. pneumoniae*) and skin and soft tissue pathogens (*S. aureus*, *E. coli* and *K. pneumoniae*) in these models. The in vivo performance of the amoxicillin/Prodrug 3 was consistent with the in vitro activity of this combination when assayed at a 2:1 ratio in the MIC assay.

In Vivo Antibacterial Activity (Oral) vs. Respiratory Tract and Skin & Skin Structure Pathogens (ED50, mg/kg)

| Pathogen | Amoxicillin | Prodrug 3 | Amoxicillin/Prodrug 3 (7/1 ratio) | Augmentin (7/1 ratio) |
|---|---|---|---|---|
| Gerbil Otitis Media Model | | | | |
| *Haemophilus influenzae* (54A1218)[2] | >50 | >25 | 8.9/1.3[1] | 9.9/1.4 |
| Murine Systemic Model | | | | |
| *Haemophilus influenzae* (54A1218) | >100 | >25 | 9.8/1.4 | 13.4/1.9 |
| *Moraxella catarrhalis* (87A1115) | >100 | >100 | 37.6/5.4 | 12.6/1.8 |
| *Staphylococcus aureus* (01A0400) | >100 | >12.5 | 30.6/4.4 | 17.8/2.5 |
| *Klebsiella pneumonaie* (53A0031) | >200 | >25 | 20.2/2.9 | 13.0/1.8 |
| *Eschericia coli* (51A0257) | >200 | >100 | 62.2/8.9 | 146/20.8 |
| Mouse Pneumonia Model | | | | |
| *Streptococcus pneumoniae* (02J1095) | 25 | >25 | 21.8/3.1 | 21.8/3.1 |
| *Streptococcus pneumoniae* (02J1016) | 3.3 | >25 | 2.66/0.38 | 2.66/0.38 |

[1]The first value indicates the amoxicillin concentration while the second value is the beta-lactamase inhibitor.
[2]Numbers in parantheses indicate Pfizer strain ID numbers.

In Vivo Antibacterial Activity (Oral) vs. Respiratory Tract and Skin & Skin Structure Pathogens (ED50, mg/kg)

| Pathogen | Amoxicillin | Prodrug 3 | Amoxicillin/Prodrug 3 (14/1 ratio) | Augmentin (14/1 ratio) |
|---|---|---|---|---|
| Gerbil Otitis Media Model | | | | |
| *Haemophilus influenzae* (54A1218) | >50 | >25 | 10.5/0.73[1] | 5.8/0.4 |
| Murine Systemic Model | | | | |
| *Haemophilus influenzae* (54A1218) | >100 | >25 | 12.3/0.88 | 37.9/2.7 |
| *Moraxella catarrhalis* (87A1115) | >100 | >100 | 42.5/3.0 | 23.6/1.7 |
| *Staphylococcus aureus* (01A0400) | >100 | >12.5 | 94.2/6.7 | 24.4/1.7 |
| *Klebsiella pneumonaie* (53A0031) | >200 | >25 | 23.4/1.7 | 23.4/1.7 |
| *Eschericia coli* (51A0257) | >200 | >100 | 134/9.6 | 196/14 |
| Mouse Pneumonia Model | | | | |
| *Streptococcus pneumoniae* (02J1095) | 25 | >25 | 23.6/1.7 | 17.8/1.3 |
| *Streptococcus pneumoniae* (02J1016) | 3.3 | >25 | 1.6/0.11 | 1.8/0.12 |

[1]The first value indicates the amoxicillin concentration while the second value is the beta-lactamase inhibitor.
[2]Numbers in parantheses indicate Pfizer strain ID numbers.

We claim:

1. A compound selected from the compounds having the structure:

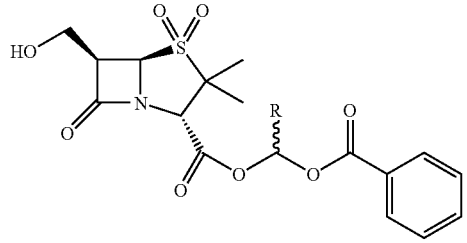

wherein R is H or methyl, wherein the compound may be in the form of a solvate.

2. A compound of claim 1 selected from:
   (a) 4-thia-1-azabicyclo[3.2.0]heptane-2-carboxylic acid, 6-(hydroxymethyl)-3,3-dimethyl-7-oxo-, (1R)-1-(benzoyloxy)ethyl ester, 4,4-dioxide, (2S,5R,6R)-;
   (b) 4-thia-1-azabicyclo[3.2.0]heptane-2-cartoxylic acid, 6-(hydroxymethyl)-3,3-dimethyl-7-oxo-, (1S)-1-(benzoyloxy)ethyl ester, 4,4-dioxide, (2S,5R,6R)-; or
   (c) 4-this-1-azabicyclo[3.2.0]heptane-2-carboxylic acid, 6-(hydroxymethyl)-3,3-dimethyl-7-oxo-, (benzoyloxy)methyl ester, 4,4-dioxide, (2S,5R,6R)-.

3. The compound of claim 1 having the structure:

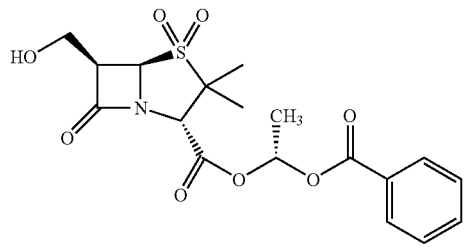

which may be in the form of a solvate.

4. A composition comprising a mixture of at least (a) 4-thia-1-azabicyclo[3.2.0]heptane-2-carboxylic acid, 6-(hydroxymethyf)-3,3-dimethyl-7-oxo-, (1R)-1-(benzoyloxy)ethyl ester, 4,4-dioxide, (2S,5R,6R)-; and (b) 4-thia-1-azabicyclo[3.2.0]heptane-2-carboxylic acid, 6-(hydroxymethyl)-3,3-dimethyl-7-oxo-, (1S)-1-(benzoyloxy)ethyl ester, 4,4-dioxide, (2S,5R,6R)-, wherein the mixture may be in the form of a solvate.

5. A composition comprising at least one compound of claim 1 in combination with at least one beta-lactam antibiotic.

6. A composition comprising at least one compound of claim 1 in combination with amoxicillin.

7. A composition comprising the compound of claim 3 in combination with at least one beta-lactam antibiotic.

8. A pharmaceutical composition comprising at least one compound of claim 1 in combination with at least one beta-lactam antibiotic, with or without one or more pharmaceutically acceptable excipients.

9. A method of treating bacterial infection comprising administering, to a mammal in need, (1) at least one compound of claim 3 and (2) at least one beta-lactam antibiotic in amounts such that the combination of (1) and (2)is effective.

10. A method of treating bacterial infection comprising administering, to a mammal in need, (1) the compound of claim 3 and (2)-a beta-lectern antibiotic in amounts such that the combination of (1) and (2) is effective.

11. A method of treating bacterial infection comprising administering, to a mammal in need thereof, a therapeutically effective amount of a pharmaceutical composition comprising:
  (a) 4-thia-1-azabicyclo[3.2.0]heptane-2-carboxylic acid, 6-(hydroxymethyi)-3,3-dimethyl-7-oxo-, (1R)-1-(benzoyloxy)ethyl ester, 4,4-dioxide, (2S,5R,6R)-, which may be in the form of a solvate; and
  (b) a beta-lactam antibiotic.

12. A method for increasing the effectiveness of a beta-lectern antibiotic comprising administering, to a mammal in need, the beta-lactam antibiotic and an effectiveness-increasing amount of at least one compound of claim 1.

13. A method for increasing the effectiveness of a beta-lactam antibiotic comprising administering, to a mammal in need, the beta-lactam antibiotic and an effectiveness-increasing amount of the compound of claim 3.

* * * * *